US010377860B2

(12) United States Patent
Kuhlman

(10) Patent No.: US 10,377,860 B2
(45) Date of Patent: Aug. 13, 2019

(54) POLYETHERIMIDES, METHODS OF MANUFACTURE, AND ARTICLES FORMED THEREFROM

(71) Applicant: SABIC GLOBAL TECHNOLOGIES B.V., Bergen op Zoom (NL)

(72) Inventor: Matthew L. Kuhlman, Evansville, IN (US)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 616 days.

(21) Appl. No.: 14/026,320

(22) Filed: Sep. 13, 2013

(65) Prior Publication Data

US 2015/0079377 A1 Mar. 19, 2015

(51) Int. Cl.

*C08G 73/10* (2006.01)
*C08L 79/08* (2006.01)
*B32B 27/28* (2006.01)
*C07D 209/48* (2006.01)

(52) U.S. Cl.

CPC ..... *C08G 73/1071* (2013.01); *C08G 73/1003* (2013.01); *C08G 73/1042* (2013.01); *C08G 73/1053* (2013.01); *C08L 79/08* (2013.01); *B32B 27/281* (2013.01); *C07D 209/48* (2013.01); *Y10T 428/31721* (2015.04)

(58) Field of Classification Search

CPC .............. C07D 209/48; C08G 73/1003; C08G 73/1042; C08G 73/1053; C08G 73/1071; C08L 79/08; B32B 27/281; Y10T 428/31721

See application file for complete search history.

(56) References Cited

U.S. PATENT DOCUMENTS 3,383,092 A 5/1968 Cazier
3,609,123 A 9/1971 Rabilloud et al.
3,671,487 A 6/1972 Abolins
3,723,373 A 3/1973 Lucas
3,787,364 A 1/1974 Wirth et al.
3,838,097 A 9/1974 Wirth et al.
3,847,867 A 11/1974 Heath et al.
4,217,438 A 8/1980 Brunelle et al.
4,417,044 A 11/1983 Parekh
4,460,778 A 7/1984 Brunelle
4,546,207 A 10/1985 Mendiratta et al.
4,550,156 A 10/1985 Gallagher
4,611,048 A 9/1986 Peters
4,757,150 A 7/1988 Guggenheim et al.
4,851,495 A 7/1989 Sheppard et al.
4,870,155 A 9/1989 Matzner et al.
4,950,729 A 8/1990 Daniels
4,988,544 A 1/1991 Cella et al.
4,999,251 A 3/1991 Foust et al.
5,028,681 A 7/1991 Peters
5,061,780 A 10/1991 Wang
5,064,921 A 11/1991 Blum et al.
5,101,006 A 3/1992 Stults et al.
5,106,938 A 4/1992 Bookbinder et al.
5,229,482 A 7/1993 Brunelle
5,246,751 A 9/1993 White et al.
5,304,627 A 4/1994 Connell et al.
5,514,813 A 5/1996 Brunelle
5,521,230 A 5/1996 Bhatia et al.
5,663,275 A 9/1997 Schmidhauser
5,830,974 A 11/1998 Schmidhauser et al.
5,856,421 A 1/1999 Schmidhauser
5,908,915 A 6/1999 Brunelle
5,917,005 A 6/1999 Brunelle et al.
6,020,456 A 2/2000 Brunelle et al.
6,235,866 B1 5/2001 Khouri et al.
6,265,521 B1 7/2001 Fyvie et al.
6,498,224 B1 12/2002 Odle et al.
6,630,568 B1 10/2003 Johnson et al.
6,657,068 B2 12/2003 Colborn et al.
6,790,934 B2 9/2004 Johnson et al.
6,849,706 B1 2/2005 Brunelle et al.
6,849,709 B2 2/2005 Brunelle et al.
6,881,815 B2 4/2005 Odle et al.
6,906,168 B2 6/2005 Khouri et al.
6,919,418 B2 7/2005 Khouri et al.
7,125,954 B2 10/2006 Guggenheim et al.

(Continued)

FOREIGN PATENT DOCUMENTS

CN 1867613 11/2006
CN 1919894 A 2/2007

(Continued)

OTHER PUBLICATIONS

International Search Report for International Application No. PCT/US2010/062191, Application Filing Date Dec. 28, 2010; dated Mar. 23, 2011, 4 pages.
Non Final Office Action, dated Apr. 17, 2015, P070122USC.
Office Action dated Feb. 24, 2015 in P070122JP.
Quafisheh et al., Potassium Phosphate as a High-Performance Solid Base in Phase-Transfer-Catalyzed Alkylation Reactions, Ind. Eng. Chem. Res. 2007, 46, 3016-3023.
Written Opinion for International Application No. PCT/US2010/062191, Application Filing Date: Dec. 28, 2010; dated Mar. 23, 2011, 6 pages.
International Search Report, International Application No. PCT/US2014/055324; International Filing Date, Sep. 12, 2014; dated Nov. 27, 2014; (P070342PCT); 4 pages.
Written Opinion of International Searching Authority, International Application No. PCT/US2014/055324; International Filing Date, Sep. 12, 2014; dated Nov. 27, 2014; (P070342PCT); 5 pages.

(Continued)

*Primary Examiner* — John D Freeman
(74) *Attorney, Agent, or Firm* — Cantor Colburn LLP

(57) ABSTRACT

A polyetherimide manufactured by reaction of an alkali metal salt of a dihydroxy aromatic compound with a bis (halophthalimide) composition comprising, based on the weight of the bis(halophthalimide) composition, from more than 45 to less than 75 weight percent of a 3,3'-bis (halophthalimide), less than 10 weight percent of a 3,4'-bis (halophthalimide), and from more than 45 to less than 75 weight percent of a (4,4'-bis(halophthalimide.

29 Claims, 1 Drawing Sheet

(56) References Cited

U.S. PATENT DOCUMENTS

| | | | | |
|---|---|---|---|---|
| 7,481,959 | B2 | 1/2009 | Richards et al. | |
| 7,605,222 | B2 | 10/2009 | Ye et al. | |
| 7,714,095 | B2 | 5/2010 | Brunelle et al. | |
| 8,309,637 | B2 | 11/2012 | Sanner et al. | |
| 8,357,773 | B1 | 1/2013 | Gallucci et al. | |
| 8,524,854 | B2 | 9/2013 | Chiong et al. | |
| 8,907,042 | B2 | 12/2014 | Kuhlman et al. | |
| 9,045,636 | B2 | 6/2015 | Gallucci et al. | |
| 9,127,128 | B2 | 9/2015 | Kuhlman et al. | |
| 9,169,358 | B2 | 10/2015 | Kuhlman et al. | |
| 2002/0091204 | A1 | 7/2002 | Fehnel et al. | |
| 2004/0019174 | A1 | 1/2004 | Ichiroku et al. | |
| 2005/0043493 | A1 | 2/2005 | Smith et al. | |
| 2005/0049392 | A1* | 3/2005 | Khouri | C08G 73/121 528/481 |
| 2006/0004223 | A1 | 1/2006 | Colborn et al. | |
| 2006/0135731 | A1 | 6/2006 | Silva et al. | |
| 2006/0135733 | A1 | 6/2006 | Khouri et al. | |
| 2006/0173158 | A1* | 8/2006 | Brunelle | C08G 73/12 528/425 |
| 2007/0043203 | A1* | 2/2007 | Ye | C08G 73/124 528/310 |
| 2009/0163691 | A1 | 6/2009 | Bernabe et al. | |
| 2011/0065891 | A1 | 3/2011 | Fang et al. | |
| 2011/0263791 | A1 | 10/2011 | Chiong et al. | |
| 2012/0029125 | A1 | 2/2012 | Gallucci et al. | |
| 2012/0251021 | A1* | 10/2012 | Swei | C09J 7/025 384/13 |
| 2012/0287555 | A1 | 11/2012 | Silvi et al. | |
| 2013/0053489 | A1 | 2/2013 | Gallucci et al. | |
| 2013/0108851 | A1 | 5/2013 | Kuhlman et al. | |
| 2013/0108852 | A1 | 5/2013 | Kuhlman et al. | |
| 2013/0260125 | A1* | 10/2013 | Ordonez | C08L 79/08 428/220 |
| 2013/0303698 | A1 | 11/2013 | Chiong et al. | |
| 2013/0344313 | A1* | 12/2013 | Ordonez | C08G 73/101 428/220 |
| 2015/0073116 | A1 | 3/2015 | Kuhlman et al. | |
| 2015/0079376 | A1 | 3/2015 | Kuhlman | |
| 2015/0080489 | A1 | 3/2015 | Kuhlman et al. | |

FOREIGN PATENT DOCUMENTS

| | | | |
|---|---|---|---|
| EP | 0132547 | B1 | 2/1989 |
| EP | 0892003 | A2 | 1/1999 |
| EP | 1403303 | B1 | 8/2008 |
| EP | 1660559 | B1 | 9/2009 |
| EP | 1426358 | B1 | 1/2010 |
| EP | 2644641 | A1 | 10/2013 |
| GB | 1392649 | | 4/1975 |
| GB | 1485172 | | 9/1977 |
| WO | 2009143440 | A1 | 11/2009 |
| WO | 2011082147 | A1 | 7/2011 |

OTHER PUBLICATIONS

English Abstract of CN 1367192 A; Date of Publication Sep. 4, 2002; 1 page.

English Abstract of CN 1560113 A; Date of Publication Jan. 5, 2005; 1 page.

English Abstract of CN 1803888 A; Date of Publication Jul. 19, 2006; 1 page.

International Search Report for International Application No. PCT/US2012/062183, Application Filing Date Oct. 26, 2012, dated Feb 28, 2013, 5 pages.

Notice of Allowance, dated May 6, 2015, P070273US.

Transmittal of the International Search Report of the International Searching Authority for PCT/US2012/062225 (P070273PCT), dated Mar. 7, 2013, 5 pages.

White, D.M., et al., "Polyetherimides Via Nitro-Dispalcement Polymerization: Monomer Synthesis and 13C-NMR Analysis of Monomers and Polymers", Journal of Polymer Science: Polymer Chemistry Edition, vol. 19, 1635-1658 (1981).

Written Opinion for International Application No. PCT/US2012/062183, Application Filing Date Oct. 26, 2012, dated Feb. 28, 2013, 13 pages.

* cited by examiner

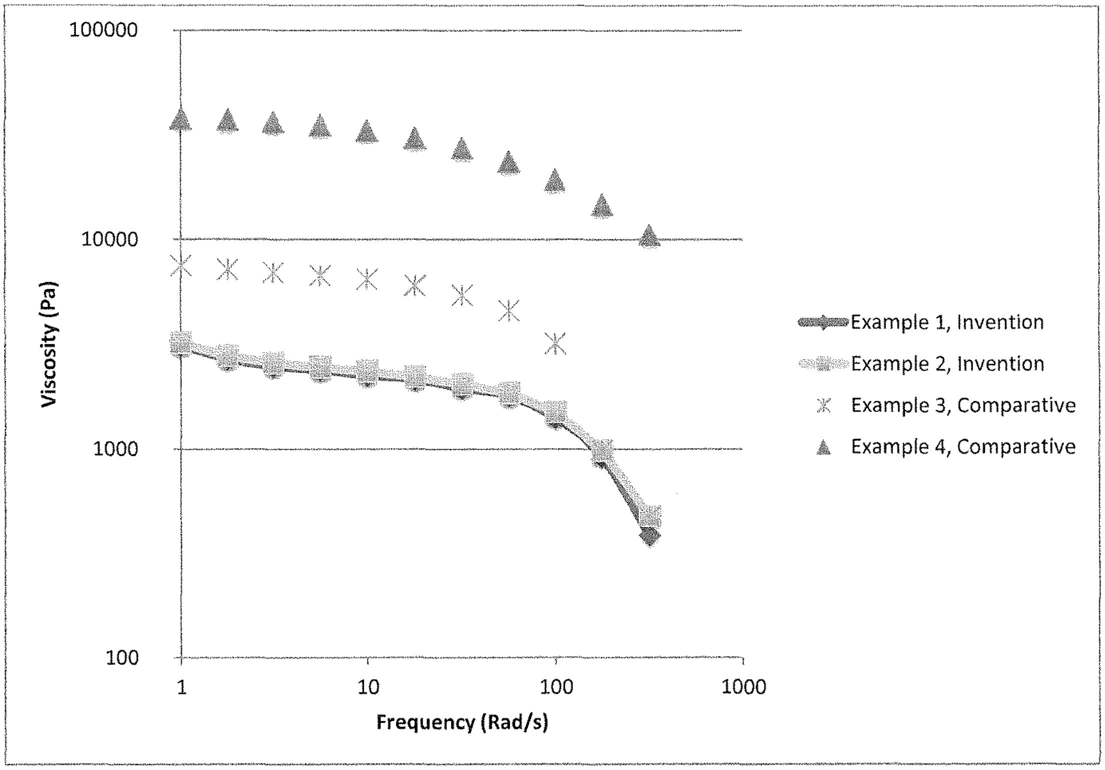
Figure 1 presents a graph of Viscosity versus Frequency measured at 340 °C for four polyetherimides (two within the scope of our invention (those used in Example 1 and Example 2), and two used in Comparative Examples 3 and 4).

POLYETHERIMIDES, METHODS OF MANUFACTURE, AND ARTICLES FORMED THEREFROM

BACKGROUND OF THE INVENTION

This disclosure relates to polyetherimides and compositions containing the polyetherimides, as well as their method of manufacture and articles formed from the polyetherimide compositions.

Polyetherimides ("PEIs") are amorphous, transparent, high performance polymers having a glass transition temperature ("Tg") of greater than 180° C. PEIs further have high strength, heat resistance, and modulus, and broad chemical resistance, and so are widely used in applications as diverse as automotive, telecommunication, aerospace, electrical/electronics, transportation, and healthcare.

Polyetherimides can be manufactured commercially by a "halo-displacement process." A halogen-substituted anhydride is reacted with a diamine to form a bishalophthalimide. The bishalophthalimide is then reacted with a metal salt of a dihydroxy compound. Despite extensive investigation into the manufacture of polyetherimides produced using the halo-displacement process, there nonetheless remains a need for further improvement. For example, some polyetherimides are currently manufactured using a 95:5 ratio of the 4-isomer to the 3-isomer of the halophthalic anhydride, which yields a product having excellent ductility. Increasing the relative ratio of the 3-isomer can enhance flow and Tg of the polyetherimides, but ratios of 90:10 or below results in a dramatic loss of ductility.

There accordingly remains a need in the art for polyetherimides and methods for the manufacture of polyetherimides having improved properties, in particular polyetherimides having improved Tg and flow, without significantly adversely affecting ductility. It would be a further advantage if such improvements were obtained without significantly adversely affecting other desirable properties of the polyetherimides, for example one or more of heat deflection temperature, Vicat, and high tensile strength at yield.

SUMMARY OF THE INVENTION

In an embodiment, a polymer composition comprises a polyetherimide having the formula

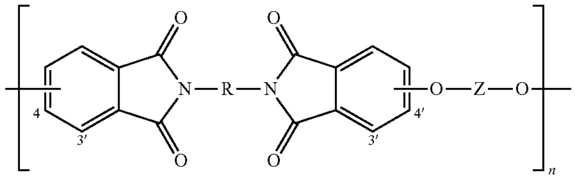

wherein n is greater than 1, each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

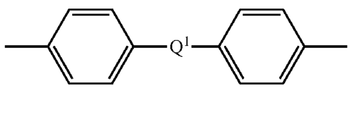

wherein $Q^1$ is selected from —O—, —S—, —C(O)—, —$SO_2$—, —SO—, and —$C_yH_{2y}$— wherein y is 1 to 5 and a halogenated derivative thereof, each Z is the same or different, and is an aromatic $C_{6-24}$ monocyclic or polycyclic moiety optionally substituted with 1 to 6 $C_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis(halophthalimide) composition, at least 90 wt. % to less than 100 wt. % of a 3,3'-bis(halophthalimide) of the formula

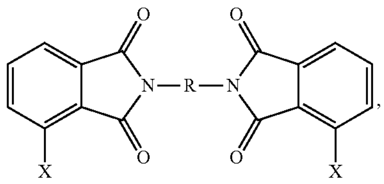, at least 1 wt. % of a 4,3'-bis(halophthalimide) of the formula

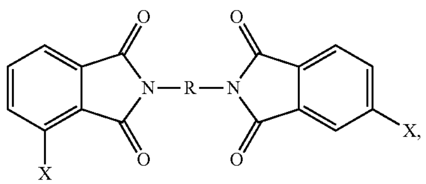, and from more than 0 wt. % to less than 2 wt. % of a 4,4'-bis (halophthalimide) of the formula

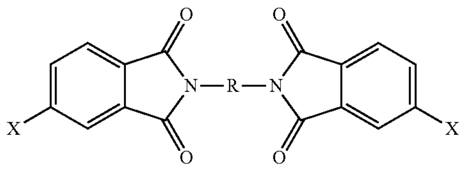

wherein each X is independently fluoro, chloro, bromo, or iodo and R is as defined above, and wherein the polyetherimide has: less than 2 weight percent content of the n=1 cyclic byproduct of 3,3-bis(halophthalimide) and an alkali metal salt of a dihydroxy aromatic compound of the formula MO—Z—OM, wherein M is an alkali metal and Z is an aromatic $C_{6-24}$ monocyclic or polycyclic moiety optionally substituted with 1 to 6 $C_{1-8}$ alkyl groups, 1 to 8 halogen atoms, or a combination thereof; a Tg greater than 230° C.; and a low shear rate viscosity: high shear rate viscosity that is at least 30% higher than the low shear rate viscosity: high shear rate viscosity of a polyetherimide made from a ClPAMI component having 3,4-ClPAMI in an amount that is less than 10%.

In another embodiment, the polyetherimide has a total cyclic content (cyclic n=1, 2, and 3) of less than 3.5 weight %, based on the total weight of the polymer, and shows no observable plate-out at molding temperature conditions.

In still another embodiment, the polyetherimide has the formula

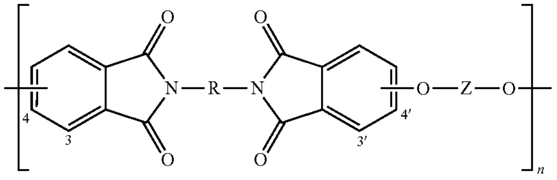

wherein n is greater than 1, each R is para-phenylene, each Z is the same or different, and is an aromatic $C_{6-24}$ monocyclic or polycyclic moiety optionally substituted with 1 to 6 $C_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the of the —O—Z—O— group being made from a bis(halophthalimide) comprising from 92 wt. % to 98 wt. % of a 3,3'-bis(chlorophthalimide) of the formula

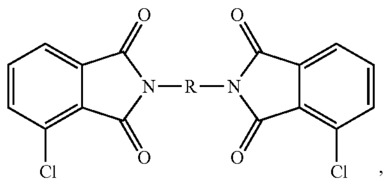
, from more than at least 1 wt. % of a 4,3'-bis(chlorophthalimide) of the formula

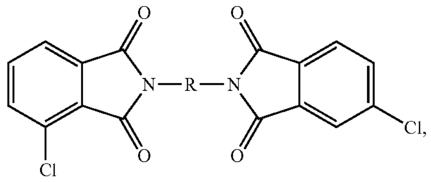
, and from more than 0 wt. % to less than 2 wt. % of a (4,4'-bis(chlorophthalimide) of the formula

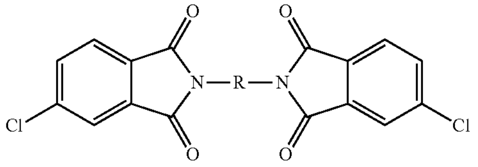

wherein R is as defined above.

In another embodiment, a method for the manufacture of the polyetherimide comprises adding the bis(halophthalimide) composition to a reactor charged with the alkali metal salt of the dihydroxy aromatic compound while maintaining at least a 50 mole % excess of the alkali metal salt of the dihydroxy aromatic compound relative to the bis(halophthalomide), and a catalytically active amount of a phase transfer catalyst, and reacting the alkali metal salt of the dihydroxy aromatic compound with the bis(halophthalimide) composition.

In a further embodiment, a method for the manufacture of the polyetherimide comprising reacting a first portion of the alkali metal salt of the dihydroxy aromatic compound with the bis(halophthalimide) composition to form a first polyetherimide composition having a first molecular weight; and then adding a second portion of the alkali metal salt of the dihydroxy aromatic compound to the first polyetherimide to form a second polyetherimide composition having a second molecular weight higher than the first molecular weight.

Compositions comprising the above polyetherimides are disclosed.

A method of manufacture of the above compositions includes melt blending the compositions of the aforementioned composition.

Articles comprising the above compositions are also disclosed. In an embodiment, the article is selected from a reflector, an optical lens, a fiber optic connector, and an adhesive, specifically an adhesive for adhering a metal to a fluoropolymer such as poly(tetrafluoroethylene). In another embodiment, an article comprises (i) a polytetrafluoroethylene substrate having a first surface, (ii) a metal substrate having a second surface, and (iii) the polymer composition of the invention situated between the polytetrafluoroethylene substrate and the metal substrate.

A method of forming the above articles includes shaping, extruding, blow molding, or injection molding the above compositions to form the article.

The invention is further illustrated by the Drawings, Detailed Description, and Examples.

BRIEF DESCRIPTION OF THE DRAWING

FIG. 1 presents a graph of Viscosity versus Frequency measured at 340° C. for four polyetherimides, two polyetherimides within the scope of our invention and two polyetherimides used in comparative examples.

DETAILED DESCRIPTION OF THE INVENTION

The invention is based, in part, on the observation that it is now possible to make a polyetherimide polymer that has a combination of (i) high glass transition temperature (Tg) properties, e.g., a Tg that is greater than 230° C. (ii) an improved viscosity that is substantially lower than viscosity of a polyetherimide made from a ClPAMI component having 3,4-ClPAMI in an amount that is less than 10%, and (iii) a very low cyclic residual content such that articles made from the polymer do not exhibit observable plate-out at molding temperature conditions. The polymer is made from specific isomers mixtures, e.g., mixtures of 3,3'-bis(halophthalimide), 4,3'-bis(halophthalimide), and 4,4'-bis(halophthalimide) isomers.

More particularly, the present invention is based, in part, on the observation that a halo-displacement process can now be used to produce polymers derived from bishalophthalimide compositions having 90 wt. % to less than 100 wt. % of the 3,3'-bis(halophthalimide), specifically from 92 wt. % to 98 wt. % of the 3,3'-bis(halophthalimide).

The present inventors have found that when the 3,3'-bis(halophthalimide) is added slowly to the $Na_2BPA$ slurry, a method they refer to as the reverse addition method (RA), this results in a reduction of the cyclic n=1 to, for example, 1.8 weight percent (wt. %), which is low enough to prevent splay and plate-out issues during molding. Also, the reduction of the cyclic n=1 improves the Tg, without a reduction in high flow of the material. The RA method can be further improved with respect to the reduction of cyclic n=1 by addition of a chain stopper, such as para-cumylphenol to the reaction; a further decrease to 1.8 wt. % to 1.3 wt. %.

Another process method (referred to herein as the modified slow salt addition or MSSA) was also discovered to reduce the cyclic n=1 level from 15 wt. % to 8 wt. % by modifying the Control process. As stated above, the Control process initially adds 95% of the salt to the ClPAMI slurry resulting in a low Mw of 20 K and then 2 to 4 mole percent of more salt is added to increase the Mw to 45-55 K. The modified process initially adds 60 to 85 mole percent, specifically 70 to 80 mole percent of the $Na_2BPA$ to the ClPAMI slurry resulting in an Mw of 7,000 amu. Once the reaction is complete, most of the balance of the $Na_2BPA$ is added (for example 13 to 38 mole %; specifically 18 to 28 mole %) to the polymer solution resulting in a Mw of 45,000 to 55,000 amu with a cyclic n=1 level of 2.75 wt. %. The cyclic n=1 can then be further reduced by adding 2 to 4 mole percent of a chain stopper, such as sodium para-cumylphenol salt, for example at the end of the reaction, resulting in cyclic n=1 of 1.8 wt. %.

In summary, two new processes are provided (RA and MSSA) to make a polyetherimide from a high 3-ClPA content monomer mixture. This method provides a polyetherimide having an increase in Tg and an order of magnitude decease in viscosity with less than 2 wt. % of cyclic n=1. This results in a dramatic improvement in the reduction of plate-out and splay when molding parts.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. Unless expressly indicated otherwise, the various numerical ranges specified in this application are approximations. The endpoints of all ranges directed to the same composition or property are inclusive of the endpoint and independently combinable.

All molecular weights in this application refer to weight average molecular weights unless indicated otherwise. All such mentioned molecular weights are expressed in amu.

The terms "a" and "an" do not denote a limitation of quantity, but rather denote the presence of at least one of the referenced item. As used herein, "combination thereof" is inclusive of one or more of the recited elements, optionally together with a like element not recited. Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and can or cannot be present in other embodiments. In addition, it is to be understood that the described element(s) can be combined in any suitable manner in the various embodiments.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The term "alkyl" includes both $C_{1-30}$ branched and straight chain, unsaturated aliphatic hydrocarbon groups having the specified number of carbon atoms, e.g., methyl, ethyl, n-propyl, i-propyl, n-butyl, s-butyl, t-butyl, n-pentyl, s-pentyl, n- and s-hexyl, n- and s-heptyl, and, n- and s-octyl. "Alkylene" means a straight or branched chain, saturated, divalent aliphatic hydrocarbon group (e.g., methylene ($—CH_2—$) or, propylene ($—(CH_2)_3—$)). "Alkoxy" means an alkyl group that is linked via an oxygen (i.e., alkyl-O—), for example methoxy, ethoxy, and sec-butyloxy groups.

"Alkenyl" means a straight or branched chain, monovalent hydrocarbon group having at least one carbon-carbon double bond (e.g., ethenyl ($—HC{=}CH_2$)).

"Cycloalkylene" means a divalent cyclic alkylene group, $—C_nH_{2n-x}$, wherein x represents the number of hydrogens replaced by cyclization(s). "Cycloalkenyl" means a monovalent group having one or more rings and one or more carbon-carbon double bond in the ring, wherein all ring members are carbon (e.g., cyclopentyl and cyclohexyl).

The term "aryl" means an aromatic moiety containing the specified number of carbon atoms, such as to phenyl, tropone, indanyl, or naphthyl.

The prefix "halo" means a group or compound including one more of a fluoro, chloro, bromo, iodo, and astatino substituent. A combination of different halo groups (e.g., bromo and fluoro) can be present. In an embodiment only chloro groups are present.

The prefix "hetero" means that the compound or group includes at least one ring that is a heteroatom (e.g., 1, 2, or 3 heteroatom(s)), wherein the heteroatom(s) is each independently N, O, S, Si, or P.

"Substituted" means that the compound or group is substituted with at least one (e.g., 1, 2, 3, or 4) substituent independently selected from a $C_{1-9}$ alkoxy, a $C_{1-9}$ haloalkoxy, a nitro ($—NO_2$), a cyano (—CN), a $C_{1-6}$ alkyl sulfonyl ($—S(=O)_2$-alkyl), a $C_{6-12}$ aryl sulfonyl ($—S(=O)_2$-aryl) a thiol (—SH), a thiocyano (—SCN), a tosyl ($CH_3C_6H_4SO_2—$), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, or a $C_{3-12}$ heteroaryl instead of hydrogen, provided that the substituted atom's normal valence is not exceeded.

All ASTM tests are based on the 2003 edition of the Annual Book of ASTM Standards unless otherwise indicated.

The polyetherimides are of formula (1)

(1)

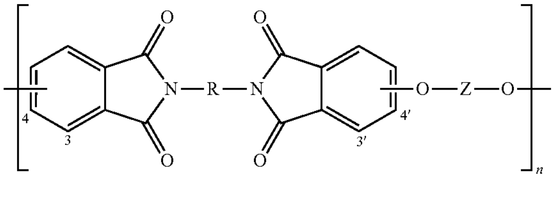

wherein n is greater than 1, for example 10 to 1,000 or more, or more specifically 10 to 500.

The group R in formula (1) is a substituted or unsubstituted divalent organic group, such as a $C_{6-30}$ or $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or a halogenated derivative thereof, or a divalent group of formula (2)

(2)

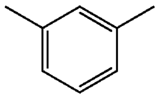, 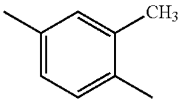,

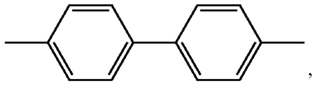,

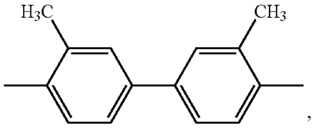,

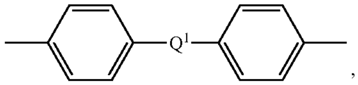, 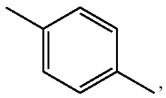,

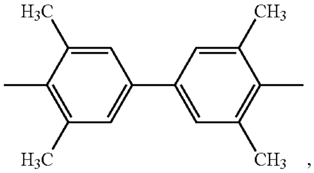,

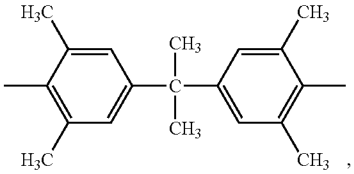, or

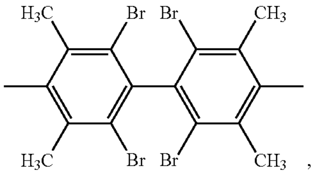, wherein $Q^1$ is —O—, —S—, —C(O)—, —$SO_2$—, —SO—, and —$C_yH_{2y}$— and a halogenated derivative thereof (which includes perfluoroalkylene groups) wherein y is an integer from 1 to 5. In a specific embodiment, R is m-phenylene or p-phenylene.

The group Z in formula (1) is also a substituted or unsubstituted divalent organic group, and can be an aromatic $C_{6-24}$ monocyclic or polycyclic moiety optionally substituted with 1 to 6 $C_{1-8}$ alkyl groups, 1 to 8 halogen atoms, or a combination thereof, provided that the valence of Z is not exceeded. Exemplary groups Z include groups derived from a dihydroxy compound of formula (3)

(3)

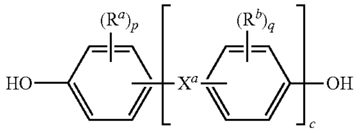

wherein $R^a$ and $R^b$ each represent a halogen atom or a monovalent hydrocarbon group and can be the same or different; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —$S(O)_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of formulas (3a)

(3a)

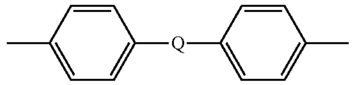

wherein Q is —O—, —S—, —C(O)—, —$SO_2$—, —SO—, and —$C_yH_{2y}$— and a halogenated derivative thereof (including a perfluoroalkylene group) wherein y is an integer from 1 to 5. In a specific embodiment, Z is derived from bisphenol A wherein Q is 2,2-isopropylidene.

In another specific embodiment, the polyetherimide comprises more than 1, specifically 10 to 1,000, or more specifically, 10 to 500 structural units, of formula (1) wherein R is a divalent group of formula (2) wherein $Q^1$ is —$C_yH_{2y}$— wherein y is an integer from 1 to 5 or a halogenated derivative thereof, and Z is a group of formula (3). In a specific embodiment, R is m-phenylene, p-arylene diphenylsulfone, or a combination thereof, and Z is 2,2-(4-phenylene)isopropylidene. For example, a polyetherimide sulfone comprises structural units of formula (1) wherein at least 50 mole % of the R groups are of formula (2) wherein $Q^1$ is —$SO_2$— and the remaining R groups are independently p-phenylene or m-phenylene or a combination comprising at least one of the foregoing; and Z is 2,2-(4-phenylene)isopropylidene.

The polyetherimide can be a copolymer, and combinations of polyetherimides can be used. In an embodiment, the polyetherimide optionally comprises additional structural imide units, for example imide units of formula (4)

(4)

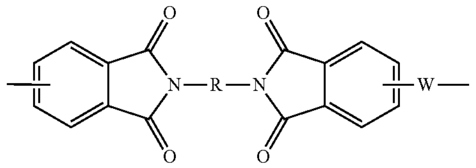

wherein R is as described in formula (1) and W is a linker of formulas (5)

(5)

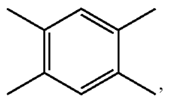, 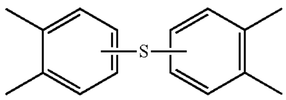, or

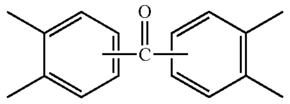

These additional structural imide units can be present in amounts ranging from 0 to 10 mole % of the total number of units, specifically 0 to 5 mole %, more specifically 0 to 2 mole %. In an embodiment no additional imide units are present in the polyetherimide.

The polyetherimides are prepared by the so-called "halo-displacement" or "chloro-displacement" method. In this method, a halophthalic anhydride of formula (6)

(6)

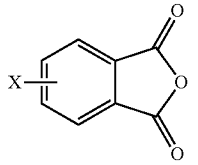

wherein X is a halogen, is condensed with an organic diamine of the formula (7)

$$H_2N—R—NH_2 \quad (7)$$

wherein R is as described in formula (1), to form a bis (halophthalimide) of formula (8)

(8)

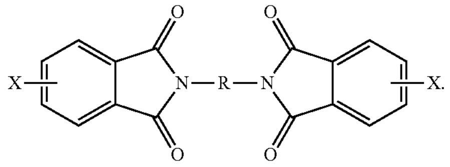

In an embodiment, X is a halogen, specifically fluoro, chloro, bromo, or iodo, more specifically chloro. A combination of different halogens can be used.

Illustrative examples of amine compounds of formula (7) include ethylenediamine, propylenediamine, trimethylenediamine, diethylenetriamine, triethylenetetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis(3-aminopropyl)amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(b-amino-t-butyl) toluene, bis(p-b-amino-t-butylphenyl) ether, bis(p-b-methyl-o-aminophenyl)benzene, bis(p-b-methyl-o-aminopentyl)benzene, 1,3-diamino-4-isopropylbenzene, bis(4-aminophenyl) ether and 1,3-bis(3-aminopropyl)tetramethyldisiloxane. Combinations of these amines can be used. Illustrative examples of amine compounds of formula (7) containing sulfone groups include diamino diphenyl sulfone (DDS) and bis(aminophenoxy phenyl) sulfones (BAPS). Combinations comprising any of the foregoing amines can be used.

In a specific embodiment diamine (7) is a meta-phenylene diamine (7a) or a para-phenylene diamine (7b)

(7a)

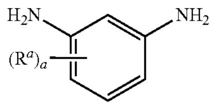

(7b)

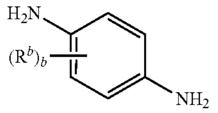

wherein $R^1$ and $R^2$ are each independently a halogen atom, nitro, cyano, $C_2$-$C_{20}$ aliphatic group, $C_2$-$C_{40}$ aromatic group, and a and b are each independently 0 to 4. Specific examples include meta-phenylenediamine (mDA), para-phenylenediamine (pDA), 2,4-diaminotoluene, 2,6-diaminotoluene, 2-methyl-4,6-diethyl-1,3-phenylenediamine, 5-methyl-4,6-diethyl-1,3-phenylenediamine, or 1,3-diamino-4-isopropylbenzene. Combinations comprising any of the foregoing amines can be used.

Condensation of halophthalic anhydride (6) and amine (7) (imidization) can be conducted in the absence or presence of a catalyst. Exemplary phase transfer catalysts for imidization include sodium phenyl phosphinate (SPP), acetic acid, hexaethylguanidinium, benzoic acid, phthalic acid, or substituted derivatives thereof. In an embodiment, sodium phenyl phosphinate is used as the imidization catalyst. The catalyst, if used, is present in an amount effective to accelerate the reaction, for example about 0.1 wt. % to 0.3 wt. % based on the weight of diamine.

The reaction is generally conducted in the presence of a relatively non-polar solvent, preferably with a boiling point above about 100° C., specifically above about 150° C., for example o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned.

The bis(halophthalimide)s (8) are generally prepared at least 110° C., specifically 150° to 275° C., more specifically 175° to 225° C. At temperatures below 110° C., reaction rates can be too slow for economical operation. Atmospheric or super-atmospheric pressures can be used, for example up to 5 atmospheres, to facilitate the use of high temperatures without causing solvent to be lost by evaporation.

The solvent, diamine (7), and halophthalic anhydride (6) can be combined in amounts such that the total solids content during the reaction to form bis(halophthalimide) (8) does not exceed about 25 wt. %, or about 17 wt. %. "Total solids content" expresses the proportion of the reactants as a percentage of the total weight comprising liquids present in the reaction at any given time.

A molar ratio of halophthalic anhydride (6) to diamine (7) of 1.98:1 to 2.04:1, specifically 2:1 is used. While other ratios can be employed, a slight excess of anhydride or diamine can be desirable. A proper stoichiometric balance between halophthalic anhydride (6) and diamine (7) is maintained to prevent undesirable by-products that can limit the molecular weight of the polymer, and/or result in polymers with amine end groups. Accordingly, in an embodiment, imidization proceeds adding diamine (7) to a mixture of halophthalic anhydride (6) and solvent to form a reaction mixture having a targeted initial molar ratio of halophthalic anhydride to diamine; heating the reaction mixture to a temperature of at least 100° C. (optionally in the presence of an imidization catalyst); analyzing the molar ratio of the heated reaction mixture to determine the actual initial molar ratio of halophthalic anhydride (6) to diamine (7); and, if necessary, adding halophthalic anhydride (6) or diamine (7) to the analyzed reaction mixture to adjust the molar ratio of halophthalic anhydride (6) to diamine (7) to 2.01 to 2.3.

After imidization, the halogen group X of bis(halophthalimide) (8)

(8)

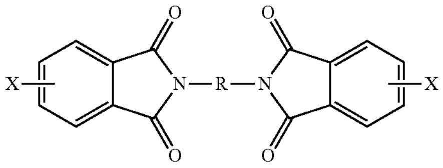

is displaced by reaction with an alkali metal salt of a dihydroxy aromatic compound of formula (9)

MO—Z—OM (9)

wherein M is an alkali metal and Z is as described in formula (1), to provide the polyetherimide of formula (1)

(1)

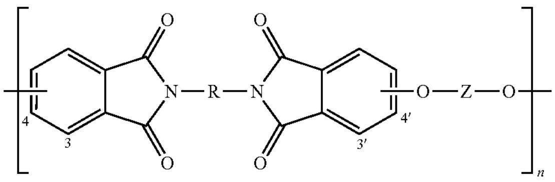

wherein n, R, and Z are as defined above.

The alkali metal M can be any alkali metal, and is typically potassium or sodium. The alkali metal salt can be obtained by reaction of the metal with an aromatic $C_{6-24}$ monocyclic or polycyclic dihydroxy compound optionally substituted with 1 to 6 $C_{1-8}$ alkyl groups, 1 to 8 halogen atoms, or a combination thereof, for example, a compound of formula (3), more specifically a dihydroxy compound corresponding to one of the groups of formulaes (3a), and still more specifically a bisphenol compound of formula (10)

(10)

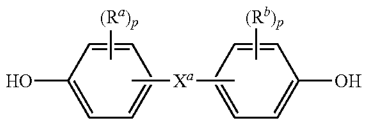

wherein $R^a$, $R^b$, and $X^a$ are as described in formula (3). For example, 2,2-bis(4-hydroxyphenyl) propane ("bisphenol A" or "BPA") can be used.

Polymerization by reaction of bis(halophthalimide) (8) with alkali metal salt (9) can be conducted in the presence or absence of phase transfer catalyst that is substantially stable under the reaction conditions used, in particular temperature. Exemplary phase transfer catalysts for polymerization include hexaalkylguanidinium and α,ω-bis(pentaalkylguanidinium)alkane salts. Both types of salts can be referred to herein as "guanidinium salts."

Polymerization is generally conducted in the presence of a relatively non-polar solvent, preferably with a boiling point above about 100° C., specifically above about 150° C., for example o-dichlorobenzene, dichlorotoluene, 1,2,4-trichlorobenzene, diphenyl sulfone, a monoalkoxybenzene such as anisole, veratrole, diphenylether, or phenetole. Ortho-dichlorobenzene and anisole can be particularly mentioned. Alternatively, a polar aprotic solvent can be used, illustrative examples of which include dimethylformamide (DMF), dimethylacetamide (DMAc), dimethylsulfoxide (DMSO), and N-methylpyrrolidinone (NMP). A combination comprising at least one of the foregoing solvents can be used.

Polymerization can be conducted at a temperature of at least 110° C., specifically 150° to 275° C., more specifically 175° to 225° C. At temperatures below 110° C., reaction rates can be too slow for economical operation. Atmospheric or super-atmospheric pressures can be used, for example up to 5 atmospheres, to facilitate the use of high temperatures without causing solvent to be lost by evaporation.

In an embodiment, alkali metal salt (9) is added to the organic solvent and the water is removed from the mixture, for example as its azeotrope. The bis(halophthalimide) (8) is then added and water removed from the mixture, for example as its azeotrope, followed by addition of a catalyst in a pre-dried solution in organic solvent. Water removal from the system can be accomplished in either batch, semi-continuous or continuous processes using means known in the art such as a distillation column in conjunction with one or more reactors. In an embodiment, a mixture of water and non-polar organic liquid distilling from a reactor is sent to a distillation column where water is taken off overhead and solvent is recycled back into the reactor at a rate to maintain or increase the desired solids concentration. Other methods for water removal include passing the condensed distillate through a drying bed for chemical or physical adsorption of water.

The molar ratio of the bis(halophthalimide) (8) to the alkali metal salt (9) can be about 1.0:0.9 to 0.9:1.0. A solids content of the bis(halophthalimide) (8) in the polymerization can be 15 wt. % to 40 wt. %, based on the total weight of the polymerization mixture.

Thus, a method for the manufacture of the polyetherimides from the bis(halophthalimide) composition comprises reacting, in the presence of a catalytically active amount of a phase transfer catalyst, the alkali metal salt (9) with a bis(halophthalimide) (8). It has been discovered by the inventors hereof that desirable properties of the polyetherimide can be obtained by careful selection of the regioisomers of the bis(halophthalimide)s (8) used to manufacture the polyetherimides. In particular, the bis(halophthalimide)s (8) can be formed from the 3-halophthalic anhydride (6a) and/or the 4-halophthalic anhydride (6b)

(6a)

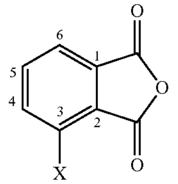

-continued (6b)

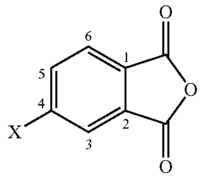

to provide the 3,3'-bis(halophthalimide) (8a), the 3,4'-bis (halophthalimide) (8b), and/or the 4,4'-bis(halophthalimide) (8c).

(8a)

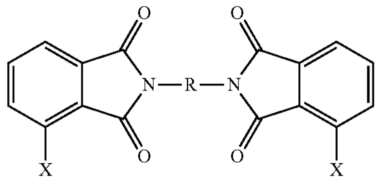

(8b)

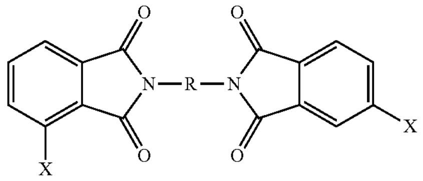

(8c)

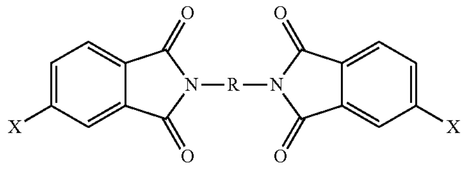

As can be seen from formula (8b), when R is symmetrical (e.g., a 1,3-phenylene or 1,4-phenylene) the 3,4'- and 3,4' isomers are the same, but when R is not symmetrical (e.g., 1-methyl-2,3-phenylene) the 3,4' and 4,3' regioisomers are not the same. Reference to the 3,4' isomer herein and in the claims specifically includes the 4,3' isomer irrespective of whether R is symmetrical. In a specific embodiment, a combination of 3-chlorophthalic anhydride (3-ClPA), 4-chlorophthalic anhydride (4-ClPA) and a diamine (7) (e.g., meta-phenylene diamine) are reacted to produce the bis (chlorophthalimide) (ClPAMI) composition as a mixture of the 3,3'-bis(chlorophthalimide) (3,3'-ClPAMI) (1,3-bis[N-(3-chlorophthalimido)]benzene), the 3,4'-bis(chlorophthalimide) (3,4'-ClPAMI) (1,1,3-bis[N-(3-chlorophthalimido, 4-chlorophthalimido)]benzene,), and the 4,4'-bis(chlorophthalimide) (4,4'-ClPAMI) (1,3-bis[N-(4-chlorophthalimido)]benzene).

The bis(halophthalimide) composition is then polymerized with an alkali metal salt of an aromatic dihydroxy compound (9) as described above. The polyetherimides manufactured from these compositions have the —O—Z—O— groups in the polyetherimide in the 3,3', 3,4', 4,3', and 4,4' positions in the same or substantially the same ratio as in the bis(halophthalimide) compositions. In an embodiment, the polyetherimide is of formula (1)

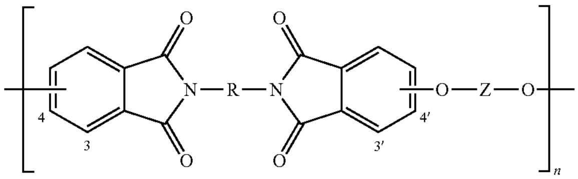

wherein n, R, and Z are as defined above. In addition, based on the total mole percent of the —O—Z—O— groups in the polyetherimide, the polyetherimides have from more than 45 to less than 75 mole percent of the divalent bonds of the —O—Z—O— groups in the 3,3' position, more than 0 and less than 10 mole percent of the divalent bonds of the —O—Z—O— groups in the 3,4', and 4',3 positions, and from more than 45 to less than 75 mole percent of the divalent bonds of the —O—Z—O— groups in the 4,4' position; or more than 45 to less than 55 mole percent of the divalent bonds of the —O—Z—O— groups are in the 3,3' position, less than 10 mole percent of the —O—Z—O— groups are in the 3,4', and 4',3 positions, and more than 45 to less than 55 mole percent of the —O—Z—O— groups are in the 4,4' position. Other mole percents, reflective of the weight percents in the bis(halophthalimide) compositions disclosed herein, can be used. Of course, these polyetherimides can have any one or more of the properties and characteristics described herein, for example one or more of less than 3,000 parts per million of a halide, based on the total parts of the polyetherimide; less than 5 wt. % of a cyclic byproduct, based on the total weight of the polyetherimide.

A chain stopper is added in the reaction. Preferably, the chain stopper is added after or before the Mw plateau is achieved and the chain stopper is from 2 to 6 mole % of a derivative of sodium phenoxide. In an embodiment, the amount of chain stopper is 3 to 4 mole %. In another embodiment, the chain stopper derivative of sodium phenoxide is sodium para cumyl phenol or sodium phenol.

The compositions can further optionally comprise a reinforcing filler, for example a flat, plate-like, and/or fibrous filler. Typically, the flat, plate-like filler has a length and width at least ten times greater than its thickness, where the thickness is from 1 to 1,000 micrometers (μm). Exemplary reinforcing fillers of this type include glass flakes, mica, flaked silicon carbide, aluminum diboride, aluminum flakes, and steel flakes; wollastonite comprising surface-treated wollastonite; calcium carbonate comprising chalk, limestone, marble and synthetic, precipitated calcium carbonates, generally in the form of a ground particulates; talc, comprising fibrous, modular, needle shaped, and lamellar talc; kaolin, comprising hard, soft, calcined kaolin, and kaolin comprising various coatings known in the art to facilitate compatibility with the polymeric matrix resin; mica; and feldspar.

Exemplary reinforcing fillers also include fibrous fillers such as short inorganic fibers, natural mineral fibrous fillers, single crystal fibers, glass fibers, ceramic fibers, and organic reinforcing fibrous fillers. Short inorganic fibers include, borosilicate glass, carbon fibers, and those derived from blends comprising at least one of aluminum silicates, aluminum oxides, magnesium oxides, and calcium sulfate hemihydrate. Single crystal fibers or "whiskers" include silicon carbide, alumina, boron carbide, iron, nickel, and copper single crystal fibers. Glass fibers, comprising glass fibers such as E, ECR, S, and NE glasses and quartz, and the like can also be used.

Such reinforcing fillers can be provided in the form of monofilament or multifilament fibers and can be used either alone or in combination with other types of fiber, through, for example, co-weaving or core/sheath, side-by-side, orange-type or matrix and fibril constructions, or by other methods known to one skilled in the art of fiber manufacture.

Typical cowoven structures include glass fiber-carbon fiber, carbon fiber-aromatic polyimide (aramid) fiber, and aromatic polyimide fiber-glass fiber. Fibrous fillers can be supplied in the form of, for example, rovings, woven fibrous reinforcements, such as 0-90 degree fabrics, non-woven fibrous reinforcements such as continuous strand mat, chopped strand mat, tissues, papers and felts and 3-dimensionally woven reinforcements, performs and braids.

The reinforcing fibers can have a diameter of 5 to 25 micrometers, specifically diameters of 9 to 15 micrometers. In preparing molding compositions, it is convenient to use reinforcing fibers such as fiberglass in the form of chopped strands of from 3 millimeters to 15 millimeters long. In articles molded from these compositions, on the other hand, shorter lengths will typically be encountered because during compounding considerable fragmentation can occur. Combinations of rigid fibrous fillers with flat, plate-like fillers can be used, for example to reduce warp of a molded article.

In some applications it can be desirable to treat the surface of the filler with a chemical coupling agent to improve adhesion to a thermoplastic resin in the composition. Examples of useful coupling agents are alkoxy silanes and alkoxy zirconates. Amino, epoxy, amide, or thio functional alkoxy silanes are especially useful. Fiber coatings with high thermal stability are preferred to prevent decomposition of the coating, which could result in foaming or gas generation during processing at the high melt temperatures required to form the compositions into molded parts.

The amount of reinforcing filler used in the polyetherimide compositions can vary widely, and is that amount effective to provide the desired physical properties and flame resistance. In some instances the reinforcing filler is present in an amount from more than 10 wt. % to 60 wt. %, more specifically 15 wt. % to 40 wt. %, and even more specifically 20 wt. % to 35 wt. %, each based on the total weight of the composition.

The polyetherimide compositions can optionally further comprise one or more other types of particulate fillers. Exemplary particulate fillers include silica powder, such as fused silica and crystalline silica; boron-nitride powder and boron-silicate powders; alumina, and magnesium oxide (or magnesia); silicate spheres; flue dust; cenospheres; aluminosilicate (atmospheres); natural silica sand; quartz; quartzite; perlite; tripoli; diatomaceous earth; synthetic silica; and combinations thereof. All of the above fillers can be surface treated with silanes to improve adhesion and dispersion with the polymeric matrix resin. When present, the amount of additional particulate filler in the polyetherimide composition can vary widely, and is that amount effective to provide the desired physical properties and flame resistance. In some instances the particulate filler is present in an amount from 1 wt. % to 80 wt. %, specifically 5 wt. % to 30 wt. %, more specifically 5 wt. % to 20 wt. %, each based on the total weight of the composition.

The polyetherimide compositions can include various additives ordinarily incorporated into polymer compositions of this type, with the proviso that any additive is selected so as to not significantly adversely affect the desired properties of the composition. Exemplary additives include catalysts (for example, to facilitate reaction between an impact modifier and the polyester), antioxidants, thermal stabilizers, light stabilizers, ultraviolet light (UV) absorbing additives, quenchers, plasticizers, lubricants, mold release agents, antistatic agents, visual effect additives such as dyes, pigments, and light effect additives, flame resistances, anti-drip agents, and radiation stabilizers. Combinations of additives can be used. The foregoing additives (except any fillers) are generally present in an amount from 0.005 wt. % to 20 wt. %, specifically 0.01 wt. % to 10 wt. %, based on the total weight of the composition.

Suitable antioxidants can be compounds such as phosphites, phosphonites and hindered phenols or mixtures thereof. Phosphorus-containing stabilizers comprising triaryl phosphites and aryl phosphonates are useful additives. Difunctional phosphorus containing compounds can also be unseeded. Preferred stabilizers can have a molecular weight greater than or equal to 300. Some exemplary compounds are tris-di-tert-butylphenyl phosphite available from Ciba Chemical Co. as IRGAPHOS® 168 and bis(2,4-dicumylphenyl)pentaerythritol diphosphite available commercially from Dover Chemical Co. as DOVERPHOS® S-9228.

Examples of phosphites and phosphonites include: triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxy pentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol tri-phosphite, tetrakis(2,4-di-tert-butyl-phenyl) 4,4'-biphenylene diphosphonite, bis(2,4-di-tert-butyl-6-methylphenyl) methyl phosphite, bis(2,4-di-tert-butyl-6-methylphenyl) ethyl phosphite, 2,2',2"-nitrilo[triethyl tris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite and 5-butyl-5-ethyl-2-(2,4,6-tri-tert-butylphenoxy)-1,3,2-dioxaphosphirane.

Combinations comprising more than one organophosphorous compound are contemplated. When used in combination, the organophosphorous compounds can be of the same type or different types. For example, a combination can comprise two phosphites or a combination can comprise a phosphite and a phosphonite. In some embodiments, phosphorus-containing stabilizers with a molecular weight greater than or equal to 300 are useful. Phosphorus-containing stabilizers, for example an aryl phosphite, may be present in the composition in an amount from 0.005 wt. % to 3 wt. %, specifically 0.01 wt. % to 1.0 wt. %, based on total weight of the composition.

Hindered phenols can also be used as antioxidants, for example, alkylated monophenols, and alkylated bisphenols or poly phenols. Exemplary alkylated monophenols include 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(alpha-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonyl phenols which are linear or branched in the side chains, for example, 2,6-di-nonyl-4-methylphenol; 2,4-dimethyl-6-(1'-methylundec-1'-yl)phenol; 2,4-dimethyl-6-(1'-methylheptadec-1'-yl)phenol; 2,4-dimethyl-6-(1'-methyltridec-1'-yl)phenol and mixtures thereof. Exemplary alkylidene bisphenols include 2,2'-methylenebis(6-tert-butyl-4-methylphenol), 2,2'-methylenebis(6-tert-butyl-4-ethylphenol), 2,2'-methylenebis[4-methyl-6-(alpha-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(alpha-methylbenzyl)-4-nonylphenol], 2,2'-methylenebis[6-(alpha, alpha-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane and mixtures thereof.

The hindered phenol compound can have a molecular weight of greater than or equal to 300 g/mole. The high molecular weight can help retain the hindered phenol moiety in the polymer melt at high processing temperatures, for example greater than or equal to 300° C. Hindered phenol stabilizers, are usually present in the composition in an amount from 0.005 wt. % to 2 wt. %, specifically 0.01 wt. % to 1.0 wt. %, based on total weight of the composition.

Examples of mold release agents include both aliphatic and aromatic carboxylic acids and their alkyl esters, for example, stearic acid, behenic acid, pentaerythritol tetrastearate, glycerin tristearate, and ethylene glycol distearate. Polyolefins such as high-density polyethylene, linear low-density polyethylene, low-density polyethylene and similar polyolefin homopolymers and copolymers can also be used a mold release agents. Mold release agents are typically present in the composition at 0.05 wt. % to 10 wt. %, based on total weight of the composition, specifically 0.1 wt. % to 5 wt. %. Preferred mold release agents will have high molecular weight, typically greater than 300, to prevent loss of the release agent from the molten polymer mixture during melt processing.

In particular, an optional polyolefin can be added to modify the chemical resistance characteristics and mold release characteristics of the composition. Homopolymers such as polyethylene, polypropylene, polybutene can be used either separately or in combination. Polyethylene can be added as high-density polyethylene (HDPE), low-density polyethylene (LDPE) or branched polyethylene. Polyolefins can also be used in copolymeric form with compounds containing carbonic acid radicals such as maleic acid or citric acid or their anhydrides, acid compounds containing acrylic acid radicals such as acrylic acid ester, and the like, as well as combinations comprising at least one of the foregoing. When present, the polyolefin, in particular HDPET, is used in an amount from more than 0 wt. % to 10 wt. %, specifically 0.1 wt. % to 8 wt. %, more specifically from 0.5 wt. % to 5 wt. %, all based on the total weight of the composition.

In some embodiments, the compositions can further include at least one additional polymer. Examples of such additional polymers include and are not limited to PPSU (polyphenylene sulfone), polyetherimides, PSU (polysulfone), PPET (polyphenylene ether), PFA (perfluoroalkoxy alkane), MFA (co-polymer of TFE tetrafluoroethylene and PFVE perfluorinated vinyl ether), FEP (fluorinated ethylene propylene polymers), PPS (poly(phenylene sulfide), PTFE (polytetrafluoroethylene), PA (polyamide), PBI (polybenzimidizole) and PAI (poly(amide-imide)), poly(ether sulfone), poly(aryl sulfone), polyphenylenes, polybenzoxazoles, polybenzthiazoles, as well as blends and co-polymers thereof. When present, the polymer is used in an amount from more than 0 wt. % to 20 wt. %, specifically 0.1 wt. % to 15 wt. %, more specifically from 0.5 wt. % to 10 wt. %, all based on the total weight of the composition. In an embodiment, no polymer other than the polyetherimide as described herein is present in the composition.

Colorants such as pigment and/or dye additives can also optionally be present. Useful pigments can include, for example, inorganic pigments such as metal oxides and mixed metal oxides such as zinc oxide, titanium dioxide, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amount from 0 wt. % to 10 wt. %, specifically 0 wt. % to 5 wt. %, based on the total weight of the composition. In some instances, where improved impact is desired, pigments such as titanium dioxide will have a mean particle size of less than 5 μm.

The composition can also optionally include a fluoropolymer in an effective amount to provide anti-drip or other beneficial properties to the resin composition. In one instance, the fluoropolymer is present in an amount 0.01 wt. % to 5.0 wt. % of the composition. Examples of suitable fluoropolymers and methods for making such fluoropolymers are set forth, for example, in U.S. Pat. Nos. 3,671,487, 3,723,373, and 3,383,092. Suitable fluoropolymers include homopolymers and copolymers that comprise structural units derived from one or more fluorinated alpha-olefin monomers, for example, $CF_2{=}CF_2$, $CHF{=}CF_2$, $CH_2{=}CF_2$ and $CH_2{=}CHF$ and fluoro propylenes such as, for example, $CF_3CF{=}CF_2$, $CF_3CF{=}CHF$, $CF_3CH{=}CF_2$, $CF_3CH{=}CH_2$, $CF_3CF{=}CHF$, $CHF_2CH{=}CHF$ and $CF_3CF{=}CH_2$.

Copolymers comprising structural units derived from two or more fluorinated alpha-olefin monomers can also be used, for example poly(tetrafluoroethylene-hexafluoroethylene), as well as copolymers comprising structural units derived from one or more fluorinated monomers and one or more non-fluorinated monoethylenically unsaturated monomers that are copolymerizable with the fluorinated monomers such as poly(tetrafluoroethylene-ethylene-propylene) copolymers. Suitable non-fluorinated monoethylenically unsaturated monomers include for example, alpha-olefin monomers such as ethylene, propylene, butene, acrylate monomers such as, methyl methacrylate, butyl acrylate, and the like, with poly(tetrafluoroethylene) homopolymer (PTFE) preferred.

The fluoropolymer can be pre-blended in some manner with a polymer such as an aromatic polycarbonate or polyetherimide resin. For example, an aqueous dispersion of fluoropolymer and a polycarbonate resin can be steam precipitated to form a fluoropolymer concentrate for use as a drip inhibitor additive in thermoplastic resin compositions, as disclosed, for example, in U.S. Pat. No. 5,521,230. Alternatively, the fluoropolymer can be encapsulated.

In some instances it is desired to have polyetherimide compositions that are essentially free of bromine and chlorine. "Essentially free" of bromine and chlorine means that the composition has less than 3 wt. % of bromine and chlorine, and in other embodiments, less than 1 wt. % bromine and chlorine by weight of the composition. In other embodiments, the composition is halogen free. "Halogen free" is defined as having a halogen content (total amount of fluorine, bromine, chlorine and iodine) of less than or equal to 1,000 parts by weight of halogen per million parts by weight of the total composition (ppm). The amount of halogen can be determined by ordinary chemical analysis such as atomic absorption.

The polyetherimide compositions can be prepared by blending the ingredients under conditions for the formation of an intimate blend. Such conditions often include melt mixing in single or twin screw type extruders, mixing bowl, or similar mixing devices that can apply a shear to the components. Twin-screw extruders are often preferred due to their more intensive mixing capability and self-wiping capability, over single screw extruders. It is often advantageous to apply a vacuum to the blend through at least one vent port in the extruder to remove volatile impurities in the composition. Often it is advantageous to dry the polyetherimide polymers prior to melting. The melt processing is often performed at 320° to 380° C. to avoid excessive polymer degradation while still allowing sufficient melting to get an intimate polymer mixture free of any unbelted components. The polymer blend can also be melt filtered using a 40 to 100 micrometer candle or screen filter to remove undesirable black specks or other heterogeneous contaminants.

In an exemplary process, the various components are placed into an extrusion compounder to produce a continuous strand that is cooled and then chopped into pellets. In another procedure, the components are mixed by dry blending, and then fluxed on a mill and comminuted, or extruded and chopped. The composition and any optional components can also be mixed and directly molded, e.g., by injection or transfer molding techniques. Preferably, all of the components are freed from as much water as possible. In addition, compounding is carried out to ensure that the residence time in the machine is short; the temperature is carefully controlled; the friction heat is utilized; and an intimate blend between the components is obtained.

The composition can then be molded in any equipment conventionally used for thermoplastic compositions, such as a Newbury or van Dorn type injection-molding machine with conventional cylinder temperatures, at 350° to 400° C., and conventional mold temperatures at 100° to 170° C.

The physical properties of the polyetherimide composition can be varied to achieve the desired performance properties.

Also, the polyetherimides can have a ratio of a low shear rate viscosity to a high shear rate viscosity that is at least 30% higher than the same ratio of the same polyetherimide manufactured using the bis(halophthalimide) composition comprising more than 10 wt. % of the 3,4'-bis(halophthalimide) each determined by parallel plate rheometry.

In a further advantageous feature, the polyetherimides can have reduced levels of cyclic byproducts arising from the intramolecular reaction of the alkali metal salt (9) and the bis(halophthalimide)s (8). In an embodiment, the polyetherimides manufactured as described above comprise, based on parts of the polyetherimide, less than 5 wt. %, specifically less than 3 wt. %, more specifically less than 1.5 wt. % of the cyclic byproducts of the alkali metal salt (9) and the bis(halophthalimide) (8), specifically the bis(chlorophthalimide).

The polyetherimides having low cyclic byproducts have no observable plate-out at molding temperature conditions, which produces molded products of higher quality and acceptability in electrical/electronics applications.

The polyetherimides can have a weight average molecular weight (Mw) of 5,000 to 100,000 grams per mole (g/mole) as measured by gel permeation chromatography (GPC). In some embodiments, the Mw can be 10,000 to 80,000. The molecular weights as used herein refer to the absolute weight averaged molecular weight (Mw), referenced to polystyrene standards.

The polyetherimides can have a glass transition temperature greater than 180° C., specifically 200° to 315° C., as measured using differential scanning calorimetry (DSC) per American Society for Testing Materials (ASTM) test D3418. In an embodiment, the polyetherimide has a glass transition temperature of 220° to 240° C., more specifically 230° to 235° C.

Also disclosed are articles comprising the above-described polyetherimide compositions. The article can be a sheet, film, multilayer sheet, multilayer film, molded part, extruded profile, coated part, or fiber. Also, the article can be a molded part having a thickness from 0.1 to 100 mm, specifically 1 to 10 mm, more specifically 1 to 5 mm.

The polyetherimide compositions can be formed into articles by any number of methods, for example, shaping, extruding (including profile extrusion), thermoforming, or molding, including injection molding, compression molding, gas assist molding, structural foam molding, and blow molding. In an embodiment, a method of forming an article comprises shaping, extruding, blow molding, or injection molding the composition to form the article. Polyetherimide compositions can also be formed into articles using thermoplastic processes such as film and sheet extrusion, for example melt casting, blown film extrusion and calendaring. Co-extrusion and lamination processes can be used to form composite multi-layer films or sheets.

Examples of applications include: food service, medical, lighting, lenses, sight glasses, windows, enclosures, safety shields, and the like. The high melt flow allows the composition to be molded into intricate parts with complex shapes and/or thin sections and long flow lengths. Examples of other articles include, but are not limited to, cookware, medical devices, trays, plates, handles, helmets, animal cages, electrical connectors, enclosures for electrical equipment, engine parts, automotive engine parts, lighting sockets and reflectors, electric motor parts, power distribution equipment, communication equipment, computers and the like, comprising devices that have molded in snap fit connectors. The polyetherimide compositions can also be made into film and sheet as well as compositions of laminate systems. Other articles include, for example, fibers, sheets, films, multilayer sheets, multilayer films, molded parts, extruded profiles, coated parts and foams: windows, luggage racks, wall panels, chair parts, lighting panels, diffusers, shades, partitions, lenses, skylights, lighting devices, reflectors, ductwork, cable trays, conduits, pipes, cable ties, wire coatings, electrical connectors, air handling devices, ventilators, louvers, insulation, bins, storage containers, doors, hinges, handles, sinks, mirror housing, mirrors, toilet seats, hangers, coat hooks, shelving, ladders, hand rails, steps, carts, trays, cookware, food service equipment, communications equipment and instrument panels.

The compositions are especially useful for articles such as reflectors, e.g., automobile reflectors, an optical lens, a fiber optic connector, and an adhesive. Where the compositions are used as an adhesive, the article comprises a first substrate having a first surface, a second substrate having a second surface, and a layer of a polymer composition comprising the polyetherimide disposed between and in contact with the first surface and the second surface. For example, the adhesive can be used to adhere two polymer substrates, two metal substrates, or a metal substrate and a polymer substrate. There is no particular limitation as to the type of metals or polymers in the substrates. In an embodiment, the adhesive is especially useful in an article having a metal substrate and a fluoropolymer substrate (such as polytetrafluoroethylene (PTFE)) substrate, and an adhesive composition comprising the poly(etherimide) disposed between a surface of the metal substrate and a surface of the fluoropolymer substrate. In a specific embodiment, an article comprises (i) a polytetrafluoroethylene substrate having a first surface, (ii) a metal substrate having a second surface, and (iii) the polymer composition of the invention, situated between the polytetrafluoroethylene substrate and the metal substrate. The adhesive layer containing the polymer composition can be in direct contact with the surfaces of the adherends, or an additional layer can be present, for example a primer.

Without further elaboration, it is believed that one skilled in the art can, using the description herein, utilize the present invention. The following examples are included to provide additional guidance to those skilled in the art of practicing the claims. Accordingly, these examples are not intended to limit the invention in any manner.

EXAMPLES

Materials used in the Examples are listed in Table 1. Amounts listed in the Examples are in weight percent (wt. %), based on the total weight of the identified composition.

TABLE 1

| Material | Chemical Description | Source |
|---|---|---|
| ClPAMI Mixture 1 | | SABIC |
| 95 wt. % 3,3' ClPAMI | 1,3-bis[N-(3-chlorophthalimido)]benzene | |
| 1 wt. % 4,4'-ClPAMI | 1,3-bis[N-(4-chlorophthalimido)]benzene | |
| 4 wt. % 3,4'-ClPAMI | 1,3-[N-(4-chlorophthalimido)][N-(3-chlorophthalimido)]benzene | |
| ClPAMI Mixture 2 | | SABIC |
| 95 wt. % 3,3' ClPAMI | 1,3-bis[N-(3-chlorophthalimido)]benzene | |
| 1 wt. % 4,4'-ClPAMI | 1,3-bis[N-(4-chlorophthalimido)]benzene | |
| 4 wt. % 3,4'-ClPAMI | 1,3-[N-(4-chlorophthalimido)][N-(3-chlorophthalimido)]benzene | |
| ClPAMI Mixture 3 | | SABIC |
| 25 wt. % 3,3' ClPAMI | 1,3-bis[N-(3-chlorophthalimido)]benzene | |
| 25 wt. % 4,4'-ClPAMI | 1,3-bis[N-(4-chlorophthalimido)]benzene | |
| 50 wt. % 3,4'-ClPAMI | 1,3-[N-(4-chlorophthalimido)][N-(3-chlorophthalimido)]benzene | |
| ClPAMI Mixture 4 | | SABIC |
| 1 wt. % 3,3' ClPAMI | 1,3-bis[N-(3-chlorophthalimido)]benzene | |
| 90 wt. % 4,4'-ClPAMI | 1,3-bis[N-(4-chlorophthalimido)]benzene | |
| 9 wt. % 3,4'-ClPAMI | 1,3-[N-(4-chlorophthalimido)][N-(3-chlorophthalimido)]benzene | |
| ClPAMI Mixture 5 | | SABIC |
| 95 wt. % 3,3' ClPAMI | 1,3-bis[N-(3-chlorophthalimido)]benzene | |
| 1 wt. % 4,4'-ClPAMI | 1,3-bis[N-(4-chlorophthalimido)]benzene | |
| 4 wt. % 3,4'-ClPAMI | 1,3-[N-(4-chlorophthalimido)][N-(3-chlorophthalimido)]benzene | |
| MPD | meta-Phenylene diamine | DuPont |
| 4-ClPA | 4-Chlorophthalic anhydride | SABIC |
| 3-ClPA | 3-Chlorophthalic anhydride | SABIC |
| $H_3PO_4$ | Phosphoric acid | Fischer |
| $Na_2BPA$ | Disodium bisphenol A | SABIC |
| oDCB | Ortho-Dichlorobenzene | Fischer |
| HEGCl | Hexaethylguanidinium chloride | Atul |
| SPP | Sodium phenyl phosphinate | Fisher |
| NaPCP | Sodium para-cumyl phenol | SABIC |

Techniques and Procedures

Gel Permeation Chromatography (GPC) Testing Procedure

The GPC samples were prepared by dissolving 5-10 milligrams (mg) of a sample in 10 milliliters (mL) of dichloromethane. Three to five drops of the polymer solution were added to a 10 mL dichloromethane solution with acetic acid (1-2 drops). The sample solution was then filtered and run, and the analysis was performed by referencing the polymer peak to the oDCB peak. The instrument was a Waters 2695 separations module, which was calibrated with polystyrene standards from Aldrich Chemical Company. The cyclics were analyzed by slicing the GPC traces for cyclics n=2 and 3, but the cyclic n=1 was resolved well enough that it could be integrated separately.

Procedure for Example 1

Preparation Procedure for a Mixture of 3,3'-ClPAMI, 3,4'-ClPAMI, and 4,4'-ClPAMI A 250-mL, three-necked flask equipped with a stopper and a gas valve was charged with 3.0 grams (0.0275 moles) of mPD, 0.204 grams (0.0011 moles) 4-ClPA, 9.839 grams (0.054 moles) of 3-ClPA, 0.014 grams (0.05 mmoles) of HEGCl, and 70 grams of oDCB. The flask was then equipped with a stir shaft and bearing, nitrogen adapter, and a Dean Stark trap receiver topped with a reflux condenser. A gentle sweep of nitrogen was established through the headspace of the vessel. The reaction was then heated to 100° C.

and then ramped to 200° C. over one hour. The oDCB was removed from the mixture until it reached 16 wt. % solids (10 grams approximately of oDCB). The random reaction of this mixture of ClPA generated a 95:4:1 ratio of 3,3'-ClPAMI, 3,4'-ClPAMI, and 4,4'-ClPAMI respectively. After 2 to 3 hours, a sample was taken: 30 mg in 20 mL of acetonitrile (sonicated 15 minutes and filtered) and analyzed on the HPLC calibrated for monoamine, (monoamine is the mono-imide of halo-phthalic anhydride with a di-amine, such as mPD) 3-ClPA, 4-ClPA, and mPD. Once the amounts of analytes were known, the appropriate correction was made from either mPD or 3-ClPA. This process was repeated until the 3-monoamine, 4-monoamine, 3-ClPA and 4-ClPA were within the specification limit of the reaction, 0.2 mole percent. The reaction was then cooled and kept under a static nitrogen atmosphere.

Isomer mixtures other than the 95:4:1 random distribution illustrated above can be produced according to techniques known in the art, for example by using a similar procedure to prepare the 3,3' and 4,4'-ClPAMI isomers separately, and/or by employing different proportions of 3- and 4-ClPA starting materials to produce a product containing a different proportion of the three isomers, then blending the products of differing isomer compositions to produce another desired proportion of isomers in a polymer mixture.

Reverse Addition (RA) Polymerization Procedure

Polyetherimides were made as follows. A 250-mL, three-necked flask equipped with a stopper and a gas valve was charged with 7.257 grams (0.0267 moles) of $Na_2BPA$, 0.2187 grams (0.0009345 moles) of NaPCP and 40 grams of oDCB. The reaction was then heated to 200° C. with a gentle nitrogen sweep, to remove some oDCB drying the mixture. oDCB was removed from the mixture until it reached 22 wt. % of solids (4 grams approximately of oDCB). Once the overheads were dry by Karl Fischer analysis (less than 50 ppm) 29 milligrams (0.109 mmoles) of HEGCl was added to the salt slurry; then the ClPAMI slurry prepared above was slowly transferred to the $Na_2BPA$ slurry vessel over 90 minutes. After 90 minutes, the solution appeared golden in color. The mixture was concentrated to 36 wt. % solids over the 90 minutes of ClPAMI addition. The mixture was sampled after 2 hours to measure Mw; then the Mw analysis was repeated every hour until the reaction plateaued (plateau=3 samples within 300 amu). If the Mw was below 45,000 amu, a correction of ClPAMI was made, until the desired Mw was reached. The reaction was then quenched with 134 mg (1 mole % respect to polymer) of $H_3PO_4$ (85% aqueous) concentrated. Once the acid was added, a nitrogen purge was added to remove any water (5 minutes). The reaction was heated for another hour. The reaction was then cooled and diluted to 10 wt. % with oDCB (approximately 70 mL). The mixture was then filtered on a Buchner funnel using a Whatman 1 micrometer GF (glass filter) disk. The golden solution was then transferred to a 1-liter separatory funnel with an equal volume of acidic water and vigorously shaken. Once the contents of the separatory funnel split into phases, the golden polymer solution was transferred to a blender with an equal volume of hexane and blended. The mixture was filtered and dried under vacuum at 165° C. for 24 hours.

Procedure for Example 2

Preparation Procedure for a Mixture of 3,3'-ClPAMI, 3,4'-ClPAMI, and 4,4'-ClPAMI A 250-mL, three-necked flask equipped with a stopper and a gas valve was charged with 3.0 grams (0.0275 moles) of mPD, 0.204 grams (0.0011 moles) 4-ClPA, 9.839 grams (0.054 moles) of 3-ClPA, 0.014 grams (0.05 mmoles) of HEGCl, 0.2187 grams (0.0009345 moles) of NaPCP and 70 grams of oDCB. Also, 0.32 grams of ULTEM 1000 grade was added to the reaction mixture. The flask was then equipped with a stir shaft and bearing, nitrogen adapter, and a Dean Stark trap receiver topped with a reflux condenser. A gentle sweep of nitrogen was established through the headspace of the vessel. The reaction was then heated to 100° C. and then ramped to 200° C. over one hour. The oDCB was removed from the mixture until it reached 28 wt. % solids (40 grams approximately of oDCB). The random reaction of this mixture of ClPA generated a 95:4:1 ratio of 3,3'-ClPAMI, 3,4'-ClPAMI, and 4,4'-ClPAMI respectively. After 2 to 3 hours, a sample was taken: 30 mg in 20 mL of acetonitrile (sonicated 15 minutes and filtered) and analyzed on the HPLC calibrated for monoamine, 3-ClPA, 4-ClPA, and mPD. Once the amounts of analytes were known, the appropriate correction was made from either mPD or 3-ClPA. This process was repeated until the 3-monoamine, 4-monoamine, 3-ClPA and 4-ClPA were within the specification limit of the reaction, 0.2 mole percent. The reaction was then cooled and kept under a static nitrogen atmosphere.

A similar procedure can be used to prepare the ClPAMI isomers separately.

Modified Slow Salt Addition (MSSA) Polymerization Procedure

Polyetherimides were made as follows. Once the mixture of 3,3'-ClPAMI, 3,4'-ClPAMI, and 4,4'-ClPAMI isomers were made, the reaction vessel was then transferred to the dry box where the salt of 6.157 grams (0.02263 moles) of $Na_2BPA$ and 0.2187 grams (0.0009345 moles) of NaPCP was added. The reaction was then heated to 200° C. with a gentle nitrogen sweep, to remove some oDCB drying the mixture. oDCB was removed from the mixture until it reached 45 wt. % solids (12 grams approximately of oDCB). Once the overheads were dry by Karl Fischer analysis (less than 50 ppm), 29 milligrams (0.109 mmoles) of HEGCl was charged to the solution; within 30 minutes the solution became brownish and finally a golden solution after 90 minutes. Then 0.890 grams (0.00327 moles) of $Na_2BPA$ were added to the reaction vessel. If the Mw was below 45,000 Daltons, a correction of $Na_2BPA$ was made, until the desired Mw was reached. The analysis was repeated every hour until the reaction plateaued (plateau=3 samples within 300 amu). The reaction was then quenched with 134 mg (1 mole % respect to polymer) of $H_3PO_4$ (85% aqueous) concentrated. Once the acid was added, a nitrogen purge was added to remove any water (5 minutes). The reaction was heated for another hour. The reaction was then cooled and diluted to 10 wt. % with oDCB (approximately 70 mL). The mixture was then filtered on a Buchner funnel using a Whatman 1 micrometer GF (glass filter) disk. The golden solution was then transferred to a 1-liter separatory funnel with an equal volume of acidic water and vigorously shaken. Once the golden polymer solution had phase split, it was transferred to a blender with an equal volume of hexane and blended. The mixture was filtered and dried under vacuum at 165° C. for 24 hours.

Procedure for Comparative Examples 3, 4, and 5

Preparation Procedure for a Mixture of 3,3'-ClPAMI, 3,4'-ClPAMI, and 4,4'-ClPAMI A 250-mL, three-necked flask equipped with a stopper and a gas valve was charged with 3.0 grams (0.0275 moles) of mPD, 5.052 grams (0.0275 moles) 4-ClPA, 5.052 grams (0.0275 moles) of 3-ClPA, 0.011 grams (0.1 mmoles) of SPP, 0.2187 grams (0.0009345 moles) of NaPCP and 60 grams of oDCB. The flask was then equipped with a stir shaft and bearing, nitrogen adapter, and a Dean Stark trap receiver topped with a reflux condenser. A gentle sweep of nitrogen was established through the head-space of the vessel. The reaction was then heated to 100° C. and then ramped to 200° C. over one hour. The temperature ramp was to 150° C., 180° C., and 200° C. The oDCB was removed from the mixture until it reached 20 wt. % to 50 wt. % solids (20 grams approximately of oDCB). The random mixture of ClPA generated a 1:2:1 ratio of 3,3'-ClPAMI, 3,4'-ClPAMI, and 4,4'-ClPAMI respectively. After 2 to 3 hours, a sample was taken: 30 mg in 20 mL of acetonitrile (sonicated 15 minutes and filtered) and analyzed on the HPLC calibrated for monoamine, 4-ClPA, and mPD. Once the amounts of analytes were known, the appropriate correction was made from either mPD or 4-ClPA. This was repeated until the 3-monoamine, 4-monoamine, 3-ClPA and 4-ClPA were within the specification limit of the reaction, 0.2 mole percent. The reaction was then cooled and stoppered.

A similar procedure can be used to prepare the ClPAMI isomers separately.

Polymerization Procedure (Control)

Polyetherimides were made as follows. Once the mixture of 3,3'-ClPAMI, 3,4'-ClPAMI, and 4,4'-ClPAMI isomers were made, the reaction vessel was then transferred to the dry box where the salt of 7.122 grams (0.0261 moles) of $Na_2BPA$ was added. The reaction was then heated to 200° C. with a gentle nitrogen sweep to remove some oDCB drying the mixture. oDCB was removed from the mixture until it reached 36 wt. % to 40 wt. % solids (20 grams approximately of oDCB). Once the overheads were dry by Karl Fischer analysis (less than 50 ppm), 71 mg (1 mole %) of HEGCl was charged to the solution; within 30 minutes the solution became brownish and finally a golden solution after 90 minutes. The mixture was sampled after 2 hours to measure Mw then the Mw analysis was repeated every hour until the reaction plateaued (plateau=3 samples within 300 Daltons). If the Mw was below 45,000 Daltons, a correction of $Na_2BPA$ was made. The reaction was then quenched with 134 mg (1 mole % respect to polymer) of $H_3PO_4$ (85% aqueous) concentrated. Once the acid was added, a nitrogen purge was added to remove any water (5 minutes). The reaction was heated for another hour. The reaction was then cooled and diluted to 10 wt. % with oDCB (approximately 70 mL). The mixture was then filtered on a Buchner funnel using a Whatman 1 micrometer glass filter disk. The golden solution was then transferred to 1-liter separatory funnel with equal volume of acidic water and vigorously shaken. Once the contents of the separatory funnel had phase split, the golden polymer solution was transferred to a blender with an equal volume of hexane and blended. The mixture was filtered and dried under vacuum at 165° C. for 24 hours.

Testing Procedures

Splay/Plate-Out Study of Cyclic n=1 from Examples 1-5

A five gram sample was placed in a 50 mL sealed test tube under an inert atmosphere of nitrogen. The test tube was placed in a heating mantle with the upper 20% of the length of the tube (still sealed) exposed to the cool air (the cooled section of the test tube allowed volatiles released from the sample to condense on the inner surface, which is referred to as plate-out). The test tube with polymer material was heated at 360° C. for 15 minutes and then the temperature was increased 5 degrees every 15 minutes up to 400° C. The tube is inspected for observable polymer plate-out and recorded.

$T_g$ Testing Procedure

Glass transition temperature ($T_g$) was measured on a 10 mg sample via differential scanning calorimetry at a heating rate of 20° C./min.

Rheology Testing Procedure

The viscosity data were measured using parallel plate rheometry at 340° C., and a viscosity ratio was calculated from readings at 1 rad/sec to 316 radian/sec. This viscosity ratio gives a measure of shear thinning or improved flow properties. The higher the viscosity ratio the higher the shear thinning, with resultant improved flow.

Examples 1-5

Purpose: The purpose of Examples 1-5 was to make polyetherimides with 3,3'-ClPAMI enriched component in an amount more than 90 wt. % and evaluate how the different polymerization methods affect the properties of the materials with the same ClPAMI isomer ratio. The performance properties of these polyetherimides are also compared with polyetherimides made with 3,3'-ClPAMI in an amount less than 90 wt. % and varying amounts of 4,4'-ClPAMI and 3,4'-ClPAMI components.

The polymers prepared were targeted for 55,000 Mw (polystyrene standards were used for calibration), but some were slightly higher and lower Mw.

The molecular weights of the polyetherimides were similar, as shown in Table 2, as evidenced by the GPC data. The PDI of the 3-ClPA enriched polymers were higher than the 1000 grade control because of the cyclic n=1 (adduct of one BPA and 3,3'-ClPAMI). The cyclic n=1 is characteristic of 3-ClPA enriched polymer systems due to the high concentration of 3,3'-ClPAMI.

TABLE 2

Analysis of Examples 1-5

| Isomer (Wt. %) | Example 1 (Inventive) | Example 2 (Inventive) | Example 3 (Comparative) | Example 4 (Comparative) | Example 5 (Comparative) |
|---|---|---|---|---|---|
| 3,3' ClPAMI | 95 | 95 | 24 | 1 | 95 |
| 3,4'-ClPAMI | 4 | 4 | 50 | 9 | 4 |
| 4,4'-ClPAMI | 1 | 1 | 26 | 90 | 1 |
| Process Type | RA | MSSA | Control | Control | Control |
| Mw | 57103 | 56377 | 54027 | 55000 | 51902 |
| Mn | 24833 | 23602 | 19837 | 24000 | 16955 |
| Polydispersity Index (PDI) | 2.30 | 2.39 | 2.72 | 2.4 | 3.06 |
| Cyclic (n = 1) (wt. %) (with NaPCP) | 1.3 | 1.5 | 1.0 | 0.01 | 3.40 |
| Total cyclic (n = 1, 2, or 3) (wt. %) (no NaPCP) | 1.8 | 4.25 | 1.8 | 0.5 | 8.50 |
| Tg (° C.) | 232 | 232 | 227 | 219 | 230 |
| Observable Plate-out | No | No | No | No | Yes |
| Viscosity (Pa), measured at | | | | | |

TABLE 2-continued

| Analysis of Examples 1-5 | | | | | |
|---|---|---|---|---|---|
| Isomer (Wt. %) | Example 1 (Inventive) | Example 2 (Inventive) | Example 3 (Comparative) | Example 4 (Comparative) | Example 5 (Comparative) |
| rad/s: | | | | | |
| 1 | 3128 | 3200 | 7484 | 38160 | 3200 |
| 2 | 2692 | 2777 | 7165 | 37625 | 2777 |
| 3 | 2484 | 2571 | 6949 | 36720 | 2571 |
| 6 | 2386 | 2455 | 6729 | 35373 | 2455 |
| 10 | 2246 | 2346 | 6436 | 33384 | 2346 |
| 18 | 2161 | 2213 | 6015 | 30808 | 2213 |
| 32 | 1955 | 2040 | 5399 | 27591 | 2040 |
| 56 | 1795 | 1851 | 4564 | 23792 | 1851 |
| 100 | 1403 | 1498 | 3185 | 19423 | 1498 |
| 178 | 915 | 984 | 984 | 14848 | 984 |
| 316 | 383 | 475 | 472 | 10597 | 475 |

Discussion

The results evidence that materials made in accordance to our invention (made from specific isomers mixtures, e.g., mixtures of 3,3'-bis(halophthalimide), 4,3'-bis(halophthalimide), and 4,4'-bis(halophthalimide) isomers) exhibited a unique combination of properties, namely (i) high glass transition temperature that was greater than 230° C. (ii) an improved viscosity that was substantially lower than viscosity of a polyetherimide made from a ClPAMI component having 3,4-ClPAMI in an amount that was less than 10% and (iii) a very low cyclic residual content such that articles made from the polymer did not exhibit observable plate-out at molding temperature conditions.

More particularly, results for Example 1 show that when the PEI was made with a mixture containing at least 90 wt. % of 3,3'-ClPAMI, and less than 5 wt. % of 3,4'-ClPAMI, and with a maximum of 2 wt. % of 4,4'-ClPAMI, the resulting PEI had a Tg of 232° C. Further the PEI exhibited increased flow, as measured by lower viscosity readings at all values from 1 rad/sec to 316 rad/sec, versus Examples 4 and 3 respectively.

Table 2 shows the improved lower viscosity exhibited by compositions of our invention at 1, 10, and 100 radians/second, as is evidenced by subtracting the Comparative Example 3 and from Inventive Examples 1 and Inventive Example 2, then dividing these viscosities of the materials with the viscosities exhibited by the materials in Comparative Example 3 and Comparative Example 4 (which did not exhibit undesired plateout properties), respectively, with the viscosities of the materials used in the Inventive Examples 1 and 2 (which also did not exhibit plateout properties). The reduction in viscosity observed by our materials ranged from 53% to approximately 93%. The method for calculating the improved viscosity can be summarized by the following formula: (% lower viscosity=100%*(Comparative Example Viscosity-Inventive Example Viscosity)/Comparative Example Viscosity).

Additionally, the Example 1 PEI made with at least 90 wt. % of 3,3'-ClPAMI, and less than 5 wt. % of 3,4'-ClPAMI, and with a maximum of 2 wt. % of 4,4'-ClPAMI using the RA polymerization method results in a total cyclic content (cyclic n=1, 2, and 3) of less than 3.5 wt. %, based on the total weight of the polymer. Also, using the RA polymerization method in Example 1 results in a cyclic n=1 wt. % of less than 1.3, based on the total weight of the polymer, in comparison to Comparative Example 5 having 3.40 wt. % of cyclic n=1 with the same ClPAMI isomer ratio. If no chain-stopper, NaPCP, was used with the RA polymerization method, then the final cyclic n=1 was less than 1.9 wt. %, based on the total weight of the polymer.

Lastly, the polyetherimide of Example 1, made with the RA polymerization method showed no observable plate-out at molding temperature conditions, whereas Example 5 with the same ClPAMI isomer had observable plate-out.

The results for Example 2 show that when the PEI was made with a mixture containing at least 90 wt. % of 3,3'-ClPAMI, and less than 5 wt. % of 3,4'-ClPAMI, and with a maximum of 2 wt. % of 4,4'-ClPAMI, the resulting PEI had a Tg of 232° C. Further the PEI exhibited increased flow, as measured by lower viscosity readings at all values from 1 rad/sec to 316 rad/sec, versus Examples 4 and 3 respectively.

Additionally, the Example 2 PEI made with at least 90 wt. % of 3,3'-ClPAMI, and less 5 wt. % of 3,4'-ClPAMI, and with a maximum of 2 wt. % of 4,4'-ClPAMI using the MSSA polymerization method results in a total cyclic wt. % of less than 3.7, based on the total weight of the polymer (cyclic n=1, 2, and 3). Also, using the MSSA polymerization method results in a cyclic n=1 wt. % of less than 1.5 (with NaPCP), based on the total weight of the polymer, in comparison to Example 5 having 3.40 wt. % of cyclic n=1 with the same ClPAMI isomer ratio. If no chain-stopper, NaPCP, was used with the MSSA polymerization method, then the final cyclic n=1 was less than 4.5 wt. %, based on the total weight of the polymer.

Lastly, the Example 2 PEI made with the MSSA (with NaPCP) polymerization method showed no observable plate-out at molding temperature conditions, whereas Example 5 with the same ClPAMI isomer had observable plate-out.

The results of Comparative Example 3 show that when the PEI was made with a mixture containing more than 47 wt. % but less than 85 wt. % of 3,4'-ClPAMI and at least 15 wt. % of 3,3'-ClPAMI, the resulting PEI had a Tg of 227° C.; whereas Examples 1 and 2 had Tg's of 232° C. Further, Comparative Example 3 exhibited a 30% higher shear rate viscosity versus Examples 1 and 2.

Additionally, the Comparative Example 3 PEI made with a mixture containing more than 47 wt. % but less than 85 wt. % of 3,4'-ClPAMI and at least 15 wt. % of 3,3'-ClPAMI using the control polymerization method resulted in a total cyclic n=1 wt. % of less than 1.1, based on the total weight of the polymer. Lastly, the Comparative Example 3 polyetherimide made with the above ClPAMI isomer ratio showed no observable plate-out at molding temperature conditions.

The results for Comparative Example 4 show that when the PEI was made with a mixture containing less than 10 wt. % of 3,4'-ClPAMI and less than 2 wt. % of 3,3'-ClPAMI, the resulting PEI had a Tg of 219° C. In comparison, Examples 1 and 2 had Tg's of 232° C. Comparative Example 4 exhibited a 60% higher shear rate viscosity versus Examples 1 and 2.

The results show that when the PEI of Comparative Example 5 was made with a mixture containing at least 90 wt. % of 3,3'-ClPAMI, and less than 5 wt. % of 3,4'-ClPAMI, and with a maximum of 2 wt. % of 4,4'-ClPAMI, the resulting PEI had a Tg of 230° C.

Additionally, the Comparative Example 5 PEI made with at least 90 wt. % of 3,3'-ClPAMI, and less than 5 wt. % of 3,4'-ClPAMI, and with a maximum of 2 wt. % of 4,4'-ClPAMI using the control polymerization method resulted in a total cyclic wt. % 5.40, based on the total weight of the polymer (cyclic n=1, 2, and 3). Also, using the control polymerization method in Comparative Example 5 resulted in a cyclic n=1 wt. % of 3.4 and 8.5% (with and without NaPCP respectively), based on the total weight of the polymer, in comparison to Examples 1 and 2 having a cyclic n=1 wt. % of less than 1.5% with the same ClPAMI isomer ratio.

Lastly, the Comparative Example 5 PEI made with the control polymerization method showed significant observable plate-out at molding temperature conditions, whereas Examples 1 and 2 with the same ClPAMI isomer had no observable plate-out.

Summary of Results

The purpose of Examples 1-5 was to make polyetherimides with 3,3'-ClPAMI enriched ClPAMI component in an amount more than 90 wt. %, evaluate how the different polymerization procedures affected the properties of the materials and compare the performance properties with polyetherimides made with 3,3'-ClPAMI in an amount less than 90 wt. % and polyetherimides made with 4,4'-ClPAMI and 3,4'-ClPAMI component in various ratios.

In summary, Inventive Examples 1 and 2 demonstrated an increase in Tg, at least 232° C., and an increased flow relative to Comparative Examples 3 and 4. Inventive Examples 1 and 2 also had significantly lower overall cyclics and cyclic n=1 as compared to Comparative Example 5. Also, the Examples 1 and 2 according to the invention had no plate-out, whereas Comparative Example 5 with the same isomer ratios of ClPAMI had significant plate-out at normal molding conditions.

All patents and references cited herein are incorporated by reference.

Embodiment 1: A polymer composition comprising a polyetherimide having the formula

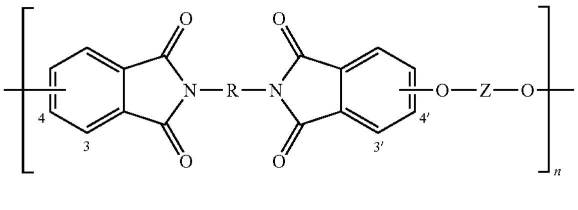

wherein n is greater than 1, each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

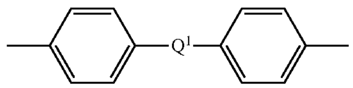

wherein $Q^1$ is selected from —O—, —S—, —C(O)—, —$SO_2$—, —SO—, and —$C_yH_{2y}$— wherein y is 1 to 5 and a halogenated derivative thereof, each Z is the same or different, and is an aromatic $C_{6-24}$ monocyclic or polycyclic moiety optionally substituted with 1 to 6 $C_{1-18}$ alkyl groups, 1 to 8 halogen atoms, or a combination thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis(halophthalimide) composition, at least 90 wt. % to less than 100 wt. % of a 3,3'-bis(halophthalimide) of the formula

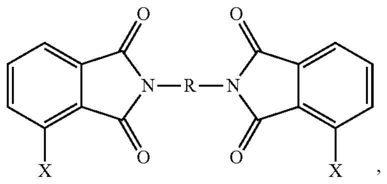

at least 1 wt. % of a 4,3'-bis(halophthalimide) of the formula

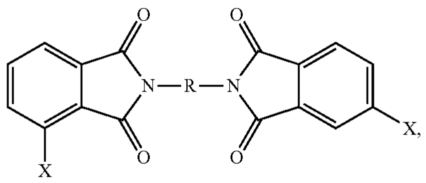

and from more than 0 wt. % to less than 2 wt. % of a 4,4'-bis (halophthalimide) of the formula

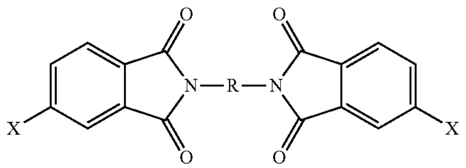

wherein each X is independently fluoro, chloro, bromo, or iodo and R is as defined above, and wherein the polyetherimide has: less than 2 weight percent content of the n=1 cyclic byproduct of 3,3-bis(halophthalimide) and an alkali metal salt of a dihydroxy aromatic compound of the formula $MO—Z—OM$, wherein M is an alkali metal and Z is an aromatic $C_{6-24}$ monocyclic or polycyclic moiety optionally substituted with 1 to 6 $C_{1-8}$ alkyl groups, 1 to 8 halogen atoms, or a combination thereof; a Tg greater than 230° C.; and a viscosity that is at least 30% lower than viscosity of a polyetherimide made from a ClPAMI component having 3,4-ClPAMI in an amount that is less than 10%.

Embodiment 2: The polymer composition of embodiment 1, wherein the composition exhibits a viscosity that is from 50% to 95% lower than the viscosity of a polyetherimide made from a ClPAMI component having 3,4-ClPAMI in an amount that is less than 10%.

Embodiment 3: The polymer composition of embodiment 1, wherein the composition exhibits a viscosity that is from 53% to 93% lower than the viscosity of a polyetherimide made from a ClPAMI component having 3,4-ClPAMI in an amount that is less than 10%.

Embodiment 4: The composition of embodiment 1, wherein the polyetherimide has a total cyclic content (cyclic n=1, 2, and 3) of less than 3.5 weight %, based on the total weight of the polymer, and shows no observable plate-out at molding temperature conditions.

Embodiment 5: The composition of embodiment 1, wherein the bis(halophthalimide) composition comprises from 92 wt. % to 98 wt. % of the 3,3'-bis(halophthalimide).

Embodiment 6: The composition of embodiment 1, wherein the polyetherimide comprises from 92 wt. % to 98 wt. % of a 3,3'-bis(chlorophthalimide) of the formula

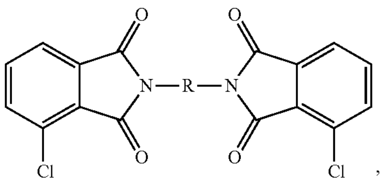

, from more than at least 1 wt. % of a 4,3'-bis(chlorophthalimide) of the formula

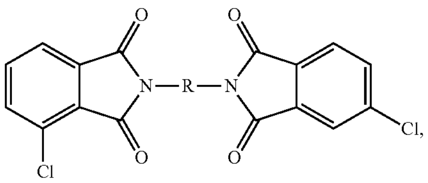

and from more than 0 wt. % to less than 2 wt. % of a (4,4'-bis (chlorophthalimide) of the formula

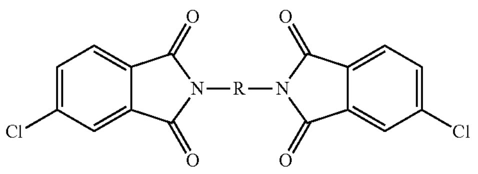

wherein each R is the same or different, and is selected from an aromatic hydrocarbon group having 6 to 30 carbon atoms, a halogenated derivative thereof, a straight or branched chain alkylene group having 2 to 10 carbon atoms, a cycloalkylene group having 3 to 10 carbon atoms, or a divalent group of the formula

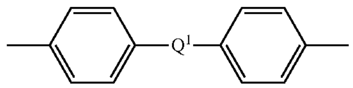

wherein $Q^1$ is selected from —O—, —S—, —C(O)—, —$SO_2$—, —SO—, and —$C_yH_{2y}$— wherein y is 1 to 5 and a halogenated derivative thereof.

Embodiment 7: The composition of embodiment 1, wherein R is a divalent radical of the formula

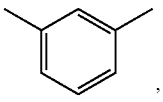

,

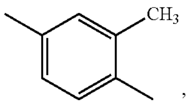

,

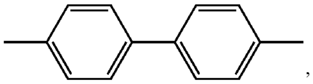

,

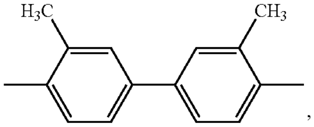

,

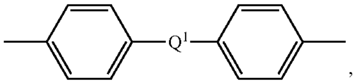

,

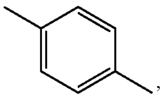

,

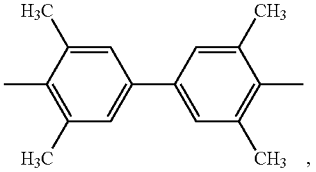

,

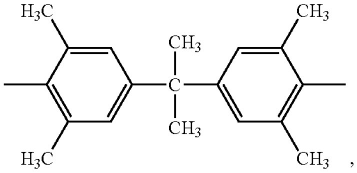

, or

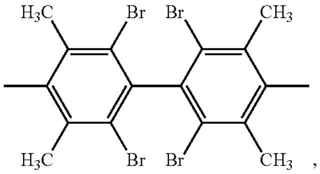

, wherein $Q^1$ is selected from —O—, —S—, —C(O)—, —$SO_2$—, —SO—, and —$C_yH_{2y}$— wherein y is an integer from 1 to 5 and a halogenated derivative thereof; and Z is a divalent group of formula

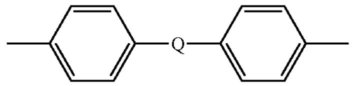

wherein Q is —O—, —S—, —C(O)—, —$SO_2$—, —SO—, or —$C_yH_{2y}$— wherein y is an integer from 1 to 5 and a halogenated derivative thereof.

Embodiment 8: The composition of embodiment 1, wherein Z is 2,2-(4-phenylene)isopropylidene and R is m-phenylene, p-phenylene diarylsulfone, or a combination thereof.

Embodiment 9: The composition of embodiment 1, further comprising an additive selected from impact modifiers, fillers, reinforcing agents, anti-oxidants, heat stabilizers, light stabilizers, ultraviolet light absorbers, plasticizers, lubricants, mold release agents, antistatic agents, colorants, blowing agents, flame retardants, anti-drip agents, and radiation stabilizers, and a combination thereof.

Embodiment 10: The composition of embodiment 1, further comprising an additive selected from an antioxidant, an ultraviolet light absorber, a mold release agent, and a combination thereof.

Embodiment 11: The composition of embodiment 1, wherein Z is 2,2-(4-phenylene)isopropylidene and R is m-phenylene, p-phenylene diarylsulfone, or a combination thereof.

Embodiment 12: A method for the manufacture of the polyetherimide composition of embodiment 1, the method comprising adding the bis(halophthalimide) composition to a reactor charged with the alkali metal salt of the dihydroxy aromatic compound and a catalytically active amount of a phase transfer catalyst while maintaining at least a 50 mole % excess of the alkali metal salt of the dihydroxy aromatic compound relative to the bis(halophthalomide) during the first 2 hours of the reaction, and reacting the alkali metal salt of the dihydroxy aromatic compound with the bis (halophthalimide) composition.

Embodiment 13: The method of embodiment 12, wherein the bis(halophthalomide) composition is added gradually.

Embodiment 14: The method of embodiment 12, wherein a chain stopper is added in the reaction.

Embodiment 15: The method of embodiment 14, wherein the chain stopper is added after or before the Mw plateau is achieved and the chain stopper is from 2 to 6 mole % of a derivative of sodium phenoxide.

Embodiment 16: The method of embodiment 14, wherein the chain stopper is sodium para cumyl phenol or sodium phenol.

Embodiment 17: The method of embodiment 15, wherein the amount of chain stopper is 3 to 4 mole %.

Embodiment 18: A method for the manufacture of the polyetherimide composition of embodiment 1, the method comprising reacting a first portion of the alkali metal salt of the dihydroxy aromatic compound with the bis(halophthalimide) composition to form a first polyetherimide composition having a first molecular weight; and then adding a second portion of the alkali metal salt of the dihydroxy aromatic compound to the first polyetherimide to form a second polyetherimide composition having a second molecular weight higher than the first molecular weight.

Embodiment 19: The method of embodiment 18, wherein the first portion of the alkali metal salt of the dihydroxy aromatic compound is 60 to 85 mole %, and the second portion is 13 to 28 mole %.

Embodiment 20: The method of embodiment 19, wherein the first portion of alkali metal salt of the dihydroxy aromatic compound is 70 to 80 mole % and the second portion is 18 to 28 mole %.

Embodiment 21: The method of embodiment 18, wherein the second salt addition is initiated once the reaction has reached 45 wt. % solids, and is a gradual addition.

Embodiment 22: The method of embodiment 18, wherein the duration of the second salt addition is from 20 minutes to 2 hours.

Embodiment 23: The method of embodiment 18, wherein the duration of the second salt addition is one hour.

Embodiment 24: The method of embodiment 18, wherein a chain stopper is added in the reaction.

Embodiment 25: The method of embodiment 24, wherein the chain stopper is added after or before the Mw plateau is achieved and the chain stopper is from 2 to 6 mole % of a derivative of sodium phenoxide.

Embodiment 26: The method of embodiment 24, wherein the chain stopper is para cumyl phenol or sodium phenol.

Embodiment 27: The method of embodiment 24, wherein the amount of chain stopper is 3 to 4 mole %.

Embodiment 28: An article comprising the composition of embodiment 1.

Embodiment 29: The article of embodiment 28, selected from a sheet, film, multilayer sheet, multilayer film, molded part, extruded profile, coated part, and fiber.

Embodiment 30: The article of embodiment 29, wherein the article is a molded part having a thickness from 1 to 5 millimeters and having a glass fiber content of up to 60 weight percent.

Embodiment 31: The article of embodiment 30, selected from a glass filled high performance article, a reflector, an optical lens, a fiber optic connector, and an adhesive.

Embodiment 32: The article of embodiment 31, the article comprising (i) a polytetrafluoroethylene substrate having a first surface, (ii) a metal substrate having a second surface, and (iii) the polymer composition, situated between the polytetrafluoroethylene substrate and the metal substrate.

Embodiment 33: The article of embodiment 31, wherein the article is a glass filled high performance article and contains from 40 wt. % to 65 wt. % glass filler.

Embodiment 34: A method of forming an article, comprising shaping, extruding, blow molding, or molding the composition of embodiment 1 to form the article.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A polymer composition comprising a polyetherimide having the formula

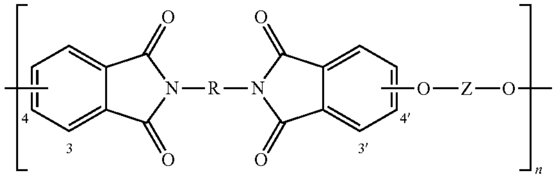

wherein n is greater than 1, each R is the same or different, and is selected from a divalent radical of the formula

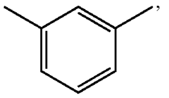,

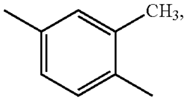

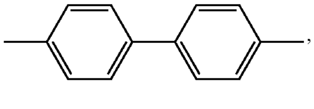,

-continued

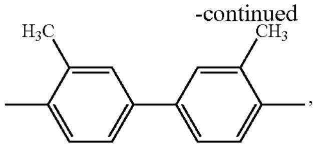

,

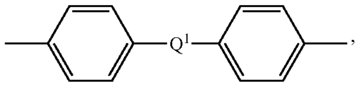

,

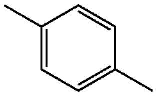

,

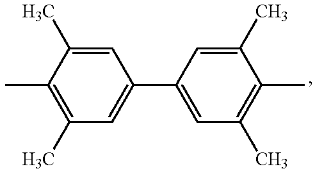

,

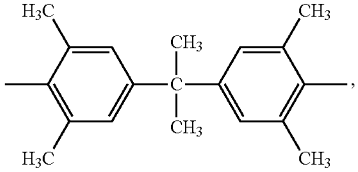

, or

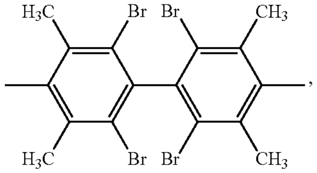

, wherein $Q^1$ is selected from —S—, —C(O)—, —$SO_2$—, —SO—, and —$C_yH_{2y}$— wherein y is an integer from 1 to 5 and a halogenated derivative thereof, each Z is the same or different, and is a divalent group of formula

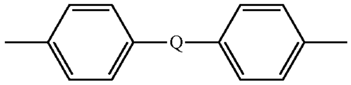

wherein Q is —O—, —S—, —C(O)—, —$SO_2$—, —SO—, or —$C_yH_{2y}$— wherein y is an integer from 1 to 5 and a halogenated derivative thereof, and the divalent bonds between the —O—Z—O— group and the phenyl substituents are in the 3,3', 3,4', 4,3', and 4,4' positions, the divalent bonds of the —O—Z—O— group being made from a bis(halophthalimide) composition comprising, based on the weight of the bis (halophthalimide) composition, at least 93 wt. % to less than 100 wt. % of a 3,3'-bis (halophthalimide) of the formula

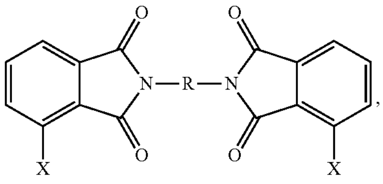

, at least 1 wt. % to less than 5 wt. % of a 4,3'-bis (halophthalimide) of the formula

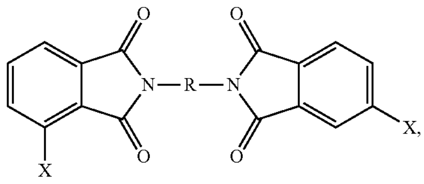

and from more than 0 wt. % to less than 2 wt. % of a 4,4'-bis(halophthalimide) of the formula

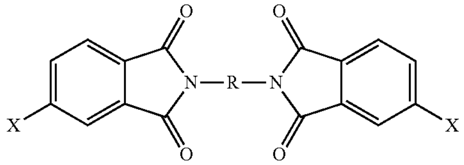

wherein each X is independently fluoro, chloro, bromo, or iodo and R is as defined above, and wherein the polyetherimide is a polymerization product of the bis(halophthalimide) composition and a alkali metal salt of a dihydroxy aromatic compound in the presence of a chain stopper comprising at least one of sodium para cumyl phenol and sodium phenol, the polyetherimide has:

less than 2 weight percent content of the n=1 cyclic byproduct of 3,3-bis(halophthalimide) and the alkali metal salt of the dihydroxy aromatic compound of the formula

—MO—Z—OM, wherein M is an alkali metal and Z is as defined above, a Tg greater than 230° C., and a total cyclic content (cyclic n=1, 2, and 3) of less than 3.5 weight %, based on the total weight of the polymer, and the polyetherimide shows no observable plate-out at molding temperature conditions.

2. The polymer composition of claim 1, wherein the bis(halophthalimide) composition comprises from 93 wt. % to 98 wt. % of the 3,3'-bis(halophthalimide).

3. The polymer composition of claim 1, wherein the bis(halophthalimide) composition comprises from 93 wt. % to 98 wt. % of a 3,3'-bis(chlorophthalimide) of the formula

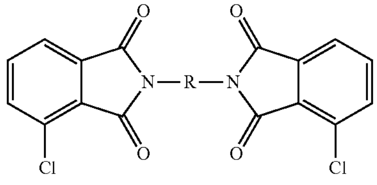

, from at least 1 wt. % to less than 5 wt. % of a 4,3'-bis (chlorophthalimide) of the formula

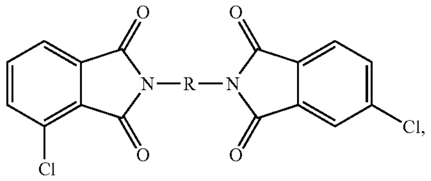

and from more than 0 wt. % to less than 2 wt. % of a (4,4'-bis(chlorophthalimide) of the formula

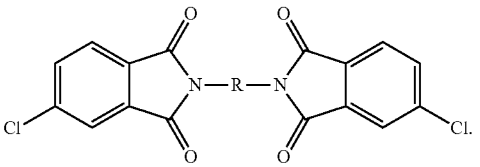

4. The polymer composition of claim 1, wherein Z is 2,2-(4-phenylene)isopropylidene and R is m-phenylene, p-phenylene, diphenylsulfone, or a combination thereof.

5. The polymer composition of claim 1, further comprising an additive selected from an impact modifier, a filler, a reinforcing agent, an anti-oxidant, a heat stabilizer, a light stabilizer, an ultraviolet light absorber, a plasticizer, a lubricant, a mold release agent, an antistatic agent, a colorant, a blowing agent, a flame retardant, an anti-drip agent, a radiation stabilizer, and a combination thereof.

6. The polymer composition of claim 1, further comprising an additive selected from an antioxidant, an ultraviolet light absorber, a mold release agent, and a combination thereof.

7. The polymer composition of claim 1, wherein the polyetherimide has a Tg greater than 230° C. and less than 240° C. as measured using differential scanning calorimetry (DSC) per American Society for Testing Materials (ASTM) test D3418.

8. The polymer composition of claim 1, wherein the polyetherimide has a Tg of greater than 230° C. and less than or equal to 235° C. as measured using differential scanning calorimetry (DSC) per American Society for Testing Materials (ASTM) test D3418.

9. The polymer composition of claim 1, wherein an amount of the chain stopper is from 2 to 6 mole % relative to the bis(halophthalimide) composition.

10. The polymer composition of claim 1, wherein an amount of the chain stopper is from 3 to 4 mole % relative to the bis(halophthalimide) composition.

11. A method for the manufacture of the polymer composition of claim 1, the method comprising adding the bis(halophthalimide) composition to a reactor charged with the alkali metal salt of the dihydroxy aromatic compound and a catalytically active amount of a phase transfer catalyst while maintaining at least a 50 mole % excess of the alkali metal salt of the dihydroxy aromatic compound relative to the bis(halophthalimide) composition during the first 2 hours of the reaction, and reacting the alkali metal salt of the dihydroxy aromatic compound with the bis(halophthalimide) composition in the presence of the chain stopper.

12. The method of claim 11, wherein the bis(halophthalimide) composition is added gradually.

13. The method of claim 11, wherein the chain stopper is added after or before a Mw plateau is achieved.

14. The method of claim 13, wherein a amount of chain stopper is 3 to 4 mole % relative to the bis(halophthalimide) composition.

15. A method for the manufacture of the polymer composition of claim 1, the method comprising reacting a first portion of the alkali metal salt of the dihydroxy aromatic compound with the bis(halophthalimide) composition to form a first polyetherimide composition having a first molecular weight; and then adding a second portion of the alkali metal salt of the dihydroxy aromatic compound to the first polyetherimide composition to form the polymer composition having a second molecular weight higher than the first molecular weight, wherein the chain stopper is added after or before a Mw plateau is achieved.

16. The method of claim 15, wherein the first portion of the alkali metal salt of the dihydroxy aromatic compound is 60 mole % to 85 mole %, and the second portion of the alkali metal salt of the dihydroxy aromatic compound is 13 to 28 mole % each relative to the bis(halophthalimide) composition.

17. The method of claim 16, wherein the first portion of the alkali metal salt of the dihydroxy aromatic compound is 70 to 80 mole % and the second portion of the alkali metal salt of the dihydroxy aromatic compound is 18 to 28 mole % each relative to the bis(halophthalimide) composition.

18. The method of claim 15, wherein the addition of the second portion of the alkali metal salt of the dihydroxy aromatic compound is initiated once the reaction has reached 45 wt. % solids, and is a gradual addition.

19. The method of claim 15, wherein the duration of the addition of the second portion of the alkali metal salt of the dihydroxy aromatic compound is from 20 minutes to 2 hours.

20. The method of claim 15, wherein the duration of the addition of the second portion of the alkali metal salt of the dihydroxy aromatic compound is one hour.

21. The method of claim 15, wherein an amount of the chain stopper is from 2 to 6 mole % relative to the bis(halophthalimide) composition.

22. The method of claim 15, wherein a amount of chain stopper is 3 to 4 mole % relative to the bis(halophthalimide) composition.

23. An article comprising the polymer composition of claim 1.

24. The article of claim 23, selected from a sheet, film, multilayer sheet, multilayer film, molded part, extruded profile, coated part, and fiber.

25. The article of claim 23, wherein the article is a molded part having a thickness from 1 to 5 millimeters and having a glass fiber content of up to 60 weight percent.

26. The article of claim 23, selected from a glass filled high performance article, a reflector, an optical lens, a fiber optic connector, and an adhesive.

27. The article of claim 23, the article comprising (i) a polytetrafluoroethylene substrate having a first surface, (ii) a metal substrate having a second surface, and (iii) the polymer composition, situated between the polytetrafluoroethylene substrate and the metal substrate.

28. The article of claim 26, wherein the article is the glass filled high performance article and contains from 40 wt. % to 65 wt. % glass filler.

29. A method of forming an article, comprising shaping, extruding, blow molding, or molding the polymer composition of claim 1 to form the article.

* * * * *